United States Patent
Chopra et al.

(12) 
(10) Patent No.: US 8,277,699 B2
(45) Date of Patent: Oct. 2, 2012

(54) PHOTOCHROMIC MATERIALS THAT INCLUDE 6-AMINO SUBSTITUTED INDENO-FUSED NAPHTHOPYRANS

(75) Inventors: Anu Chopra, Pittsburgh, PA (US); David B. Knowles, Apollo, PA (US); Huayun Yu, Monroeville, PA (US)

(73) Assignee: Transistions Optical, Inc., Pinellas Park, FL (US)

( * ) Notice: Subject to any disclaimer, the term of this patent is extended or adjusted under 35 U.S.C. 154(b) by 0 days.

(21) Appl. No.: 13/096,592

(22) Filed: Apr. 28, 2011

(65) Prior Publication Data

US 2012/0053341 A1 Mar. 1, 2012

Related U.S. Application Data

(60) Provisional application No. 61/329,737, filed on Apr. 30, 2010.

(51) Int. Cl.
*G02B 5/23* (2006.01)
*C07C 205/00* (2006.01)

(52) U.S. Cl. .......... 252/586; 351/163; 544/79; 544/150; 546/282.7; 549/384; 568/632; 568/713

(58) Field of Classification Search .................. 252/582, 252/583, 586; 428/411.1, 423.1, 446, 500; 544/31, 99, 149, 154, 338, 401, 79, 150; 546/15, 195, 167, 282.7; 549/41, 214, 341, 549/356, 381, 382, 428, 384; 568/632, 713; 351/163

See application file for complete search history.

(56) References Cited

U.S. PATENT DOCUMENTS

| | | | |
|---|---|---|---|
| 5,645,767 | A | 7/1997 | Van Gemert |
| 5,651,923 | A | 7/1997 | Kumar et al. |
| 6,025,026 | A | 2/2000 | Smith et al. |
| 6,068,797 | A | 5/2000 | Hunt |
| 6,113,814 | A | 9/2000 | Van Gemert et al. |
| 6,150,430 | A | 11/2000 | Walters et al. |
| 6,555,028 | B2 | 4/2003 | Walters et al. |
| 2003/0165686 | A1 | 9/2003 | Blackburn et al. |
| 2007/0138449 | A1* | 6/2007 | Chopra et al. ................ 252/586 |
| 2007/0278461 | A1 | 12/2007 | Petrovskaia et al. |
| 2008/0103301 | A1 | 5/2008 | Chopra et al. |

FOREIGN PATENT DOCUMENTS

| | | | |
|---|---|---|---|
| JP | 2001-011067 | * | 1/2001 |
| WO | 9828289 A1 | | 7/1998 |
| WO | 9923071 A1 | | 5/1999 |

* cited by examiner

*Primary Examiner* — Bijan Ahvazi
(74) *Attorney, Agent, or Firm* — Deborah M. Altman; Frank P. Mallak

(57) ABSTRACT

The present invention relates to photochromic materials that include certain indeno-fused naphthopyrans. The indeno-fused naphthopyrans have an amino group (e.g., a piperidino or morpholino group) bonded to the 6-position and an optional halo group (e.g., fluoro) bonded to the 11-position thereof. The photochromic materials of the present invention may have a closed-form electromagnetic radiation absorption spectrum that is shifted to longer wavelengths (e.g., wavelengths of greater than 390 nm), relative to comparable photochromic materials. The present invention also relates to optical elements, such as eyeglasses, that include the photochromic materials of the present invention.

17 Claims, 2 Drawing Sheets

PHOTOCHROMIC MATERIALS THAT INCLUDE 6-AMINO SUBSTITUTED INDENO-FUSED NAPHTHOPYRANS

CROSS REFERENCE TO RELATED APPLICATIONS

This application claims the benefit of priority of U.S. Provisional Patent Application No. 61/329,737, filed Apr. 30, 2010, which is incorporated herein by reference in its entirety.

FIELD OF THE INVENTION

The present invention relates to photochromic materials that include one or more photochromic indeno-fused naphthopyran materials. The indeno-fused naphthopyran photochromic materials of the present invention have an amino group (e.g., a piperidenyl group) bonded to the 6-position thereof, and an optional halo group (e.g., a fluoro group) bonded to the 11-position thereof. The indeno-fused naphthopyran photochromic materials of the present invention may have a closed-form electromagnetic radiation absorption spectrum that is shifted to longer wavelengths. In addition, the present invention relates to photochromic articles that include such photochromic materials.

BACKGROUND OF THE INVENTION

In response to certain wavelengths of electromagnetic radiation (or "actinic radiation"), photochromic materials, such as indeno-fused naphthopyrans, typically undergo a transformation from one form or state to another form, with each form having a characteristic or distinguishable absorption spectrum associated therewith. Typically, upon exposure to actinic radiation, many photochromic materials are transformed from a closed-form, which corresponds to an unactivated (or bleached, e.g., substantially colorless) state of the photochromic material, to an open-form, which corresponds to an activated (or colored) state of the photochromic material. In the absence of exposure to actinic radiation, such photochromic materials are reversibly transformed from the activated (or colored) state, back to the unactivated (or bleached) state. Compositions and articles, such as eyewear lenses, that contain photochromic materials typically display colorless (e.g., clear) and colored states that correspond to the colorless and colored states of the photochromic materials contained therein.

The amount of a photochromic material required to achieve a desired optical effect when incorporated into a composition or article typically depends, at least in part, on the amount of actinic radiation that the photochromic material is capable of absorbing on a per molecule basis. The amount of actinic radiation that a particular photochromic material absorbs on a per molecule basis is quantitatively referred with regard to the molar absorption coefficient (or "extinction coefficient") of the photochromic material. Photochromic materials having a relatively high molar absorption coefficient are more likely to transform from a closed-form to an open-form upon exposure to actinic radiation, than photochromic materials having a relatively lower molar absorption coefficient. Correspondingly, photochromic materials having a higher molar absorption coefficient may be used in lower concentrations in photochromic compositions and articles, than photochromic materials having a lower molar absorption coefficient, without compromising the desired optical effect.

In some applications, the amount of photochromic material that may be used or incorporated into an article may be limited for reasons including, for example, physical dimensions, solubility and/or economics. Articles having limited physical dimensions (e.g., very thin articles) may be capable of having incorporated therein only a limited and relatively low amount of photochromic material. Articles fabricated from materials in which the photochromic material has low solubility, may be capable of having incorporated therein only a limited and relatively low amount of photochromic material. Some photochromic materials are expensive, and in light of economic considerations relating to cost minimization, it may be desirable to incorporate lower amounts of photochromic material into the article. As such, photochromic materials having higher molar absorption coefficients may be desirable in applications requiring lower or minimum levels of photochromic material incorporation.

Photochromic materials, as discussed previously, are typically transformed from a closed-form (e.g., a bleached form) to an open form (e.g., a colored form) when exposed to certain wavelengths of electromagnetic radiation. In particular, many conventional photochromic materials typically undergo the closed-form to open-form transformation when exposed to electromagnetic radiation having wavelengths ranging from about 320 nanometers (nm) to about 390 nm. Such conventional photochromic materials may not be adequate for use in environments that are substantially shielded from electromagnetic radiation having wavelengths ranging from about 320 nm to about 390 nm. Certain transparencies, such as automotive windshields absorb (or act as a shield relative to) electromagnetic wavelengths in the range of 320 nm to 390 nm. As such, photochromic articles, such as photochromic eyewear, that include conventional photochromic materials, typically do not adequately undergo the closed-form (clear) to open-form (colored) transformation within the passenger compartment of an automobile (i.e., behind the windshield), because the windshield substantially absorbs electromagnetic radiation in the 320 to 390 nm wavelength range.

It may be desirable to develop photochromic materials having a closed-form absorption spectrum for electromagnetic radiation that is shifted to longer wavelengths (i.e., "bathochromically shifted"). A photochromic material having a bathochromically shifted closed-form absorption spectrum, will typically undergo the desired closed-form to open-form transformation at longer wavelengths than a conventional photochromic material. As such, in environments that are substantially shielded from electromagnetic radiation having wavelengths ranging from about 320 nm to about 390 nm (e.g., behind an automotive windshield), it may be desirable to employ photochromic materials having a closed-form absorption spectrum that is bathochromically shifted to wavelengths greater than 390 nm, which would then be capable of undergoing the desired closed-form to open-form transformation (at wavelengths greater than 390 nm).

United States Patent Application Publication No. US 2008/0103301 A1 discloses indeno-fused naphthopyrans having an electron-withdrawing, non-conjugated group bonded to the 11-position thereof.

United States Patent Application Publication No. 2007/0278461 A1 discloses indeno-fused naphthopyrans having a haloalkyl group bonded to the 13-position thereof.

SUMMARY OF THE INVENTION

In accordance with the present invention, there is provided a photochromic material that includes an indeno-fused naphthopyran comprising, an amino group bonded to the 6-position of the indeno-fused naphthopyran, the amine-nitrogen of the amino group being bonded to the 6-position, the amino group being selected from the group consisting of secondary amines and tertiary amines, and an optional halo group bonded to the 11-position of the indeno-fused naphthopyran, wherein the 13-position of the indeno-fused naphthopyran is substantially free of spiro-substituents, and haloalkyl groups and perhalo groups.

As used herein and the claims, the articles "a," "an," and "the" include plural referents unless otherwise expressly and unequivocally limited to one referent.

As used herein and in the claims, the term "actinic radiation" means electromagnetic radiation that is capable of transforming a photochromic material from one form or state to another.

As used herein, the term "photochromic" means having an absorption spectrum for at least visible radiation that varies in response to absorption of at least actinic radiation. Further, as used herein the term "photochromic material" means any substance that is adapted to display photochromic properties, i.e. adapted to have an absorption spectrum for at least visible radiation that varies in response to absorption of at least actinic radiation.

The term "closed-form absorption spectrum," as used herein and in the claims, means the absorption spectrum of a photochromic material in the closed-form or unactivated state of the photochromic material, and more particularly, the wavelength(s) of electromagnetic radiation that cause a photochromic material to undergo the desired closed-form to open-form transformation. As used herein and in the claims, the term "bathochromically shifted" with regard to the closed-form absorption spectrum of a photochromic material, means the closed-form absorption spectrum of the photochromic material is shifted to longer wavelengths.

As used herein and in the claims the term "tertiary amine" is inclusive of, but not limited to, aliphatic amines, such as dimethyl amino, cyclic amines, such as piperidenyl groups or moieties (e.g.,

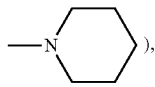

and morpholinyl groups or moieties (e.g.,

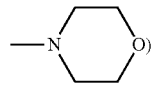

which may be substituted.

As used herein and the claims, the terms "group" or "groups" when used in relation to a chemical compound and/or representative chemical structure/formula, mean an arrangement of one or more atoms.

Other than in the operating examples, or where otherwise indicated, all numbers expressing quantities of ingredients, reaction conditions, and so forth used in the specification and claims are to be under stood as modified in all instances by the term "about."

DETAILED DESCRIPTION OF THE INVENTION

Figure 1:
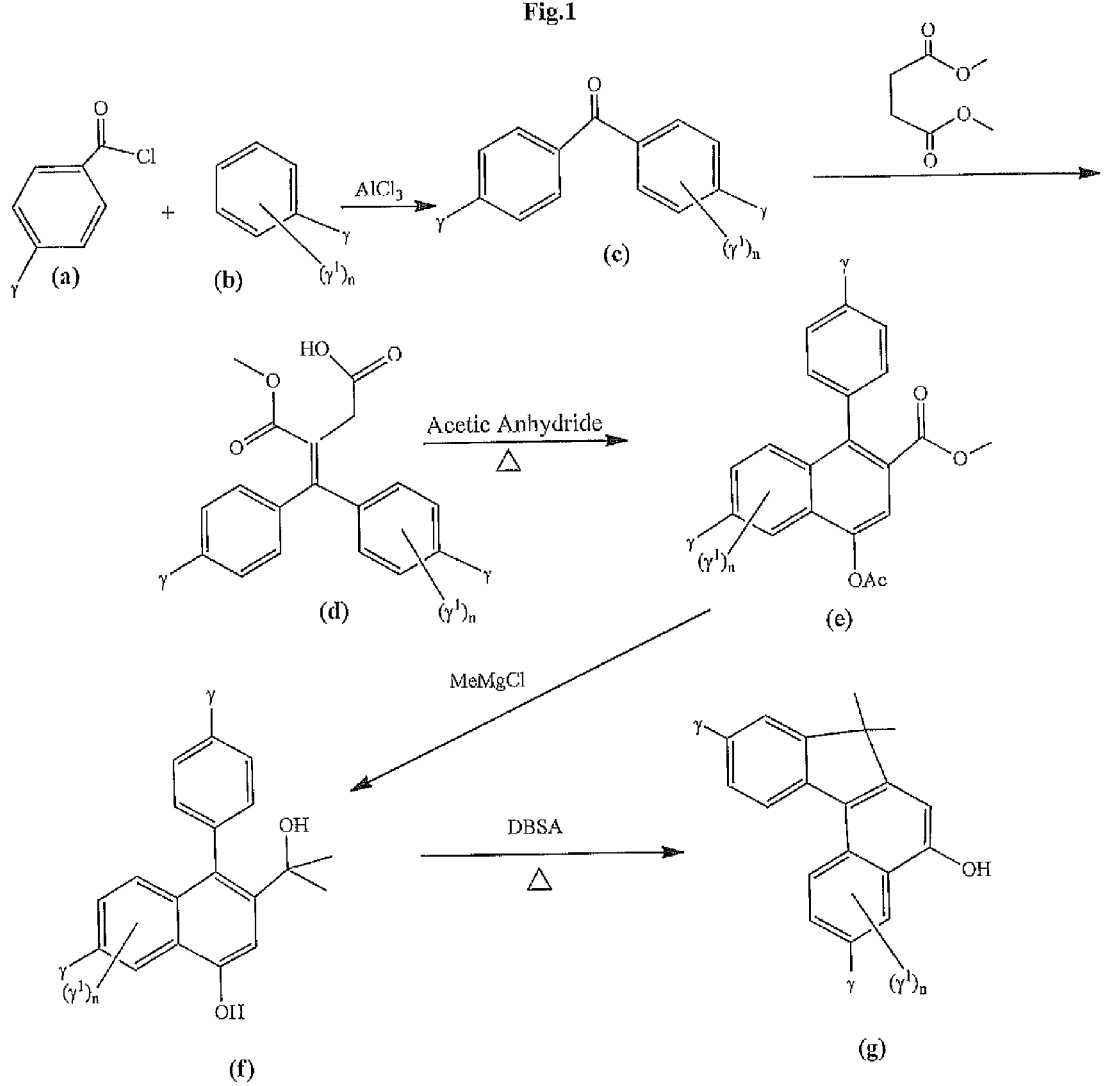
FIG. 1 is a representative schematic diagram of a reaction scheme for making an intermediate material that may be used in forming photochromic materials according to the present invention.

The photochromic material of the present invention includes an indeno-fused naphthopyran, having certain groups bonded to at least the 6-position and optionally at the 11-position of the indeno-fused naphthopyran. The various positions (e.g., 11-position) refer to the ring atoms of the indeno-fused naphthopyran, to which certain groups may be bonded. In an embodiment of the present invention, and for purposes of illustration and reference, the indeno-fused naphthopyran may be selected from: an indeno[2',3':3,4]naphtho[1,2-b]pyran, represented by the following general Formula-(I); an indeno[1',1':4,3]naphtho[2,1-b]pyran represented by the following general Formula-(II); and/or an indeno[3',2':3,4]naphtho[1,2-b]pyran, represented by general Formula (II'), in which the ring atoms are numbered as shown (in both formulas).

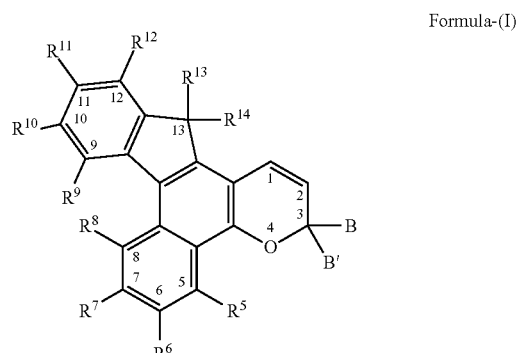

Formula-(I)

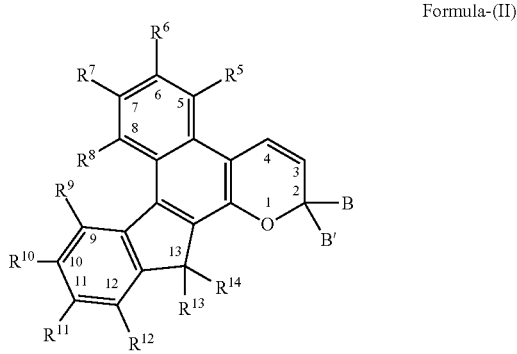

Formula-(II)

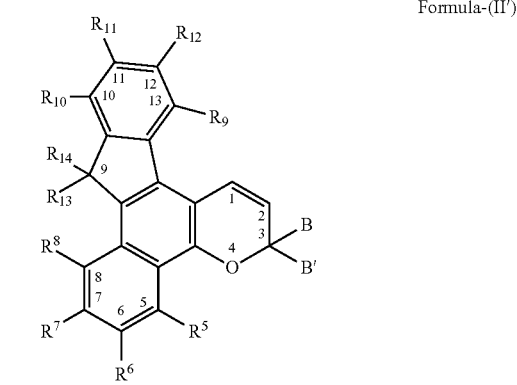

Formula-(II')

With the indeno-fused naphthopyrans represented by Formulas (I), (II) and (II'), for example, ring atom 11 is the 11-position (or position-11) of the indeno-fused naphthopyran, to which a halogroup (e.g., as represented by $R^{11}$) is bonded, as will be discussed in further detail herein. The various groups or substituents of the indeno-fused naphthopyrans represented by Formulas (I), (II) and (II') (e.g., B, B', and $R^5$ through $R^{14}$) will be described in further detail herein.

The indeno-fused naphthopyran of the photochromic material of the present invention may have a halo group bonded to the 11-position of the indeno-fused naphthopyran. The halo group bonded to the 11-position of the indeno-fused naphthopyran may be selected from fluoro (F), chloro (Cl), bromo (Br) or iodo (I). In an embodiment, the halo group bonded to the 11-position of the indeno-fused naphthopyran is selected from fluoro (F) or chloro (Cl). In a further embodiment, the halo group bonded to the 11-position of the indeno-fused naphthopyran is selected from fluoro (F).

The halo group may be bonded (i.e., covalently bonded) directly to the 11-position of the indeno-fused naphthopyran, and the 11-position of the indeno-fused naphthopyran is free of a linking group (including divalent linking groups and higher/polyvalent linking groups) interposed between the 11-position and the halo group. For example, the 11-position is free of linking groups, such as, alkylene groups (e.g., $—CH_2—$), alkenylene groups (e.g., $—CH=CH—$), alkynylene groups (e.g., $—C≡C—$), arylene groups (e.g., $—C_6H_4—$, and $—C_6H_4—C_6H_4—$).

The indeno-fused naphthopyrans of the present invention are also free of a pi-conjugation extending group bonded to the 11-position. As used herein, the term "pi-conjugation extending group" means a group having at least one pi-bond (π-bond) (e.g., a double bond and/or a triple bond) in conjugation with the pi-conjugated system of the indeno-fused naphthopyran. As would be recognized by a skilled artisan, if a pi-conjugation extending group were bonded to the 11-position of the indeno-fused naphthopyran, the pi-electrons in the pi-conjugated system of the indeno-fused naphthopyran would be de-localized over the combined pi-system of the indeno-fused naphthopyran and the pi-conjugation extending group bonded to the 11-position thereof. Conjugated bond systems include those represented by an arrangement of at least two double or triple bonds separated by one single bond, that is a system containing alternating double (and/or triple) bonds and single bonds, wherein the system contains at least two double (and/or triple) bonds. Examples of pi-conjugation extending groups, which the 11-position of the indeno-fused naphthopyran of the present invention is free of, include but are not limited to: substituted and unsubstituted alkenyl groups (e.g., substituted and unsubstituted $C_2-C_{20}$ alkenyl groups); substituted and unsubstituted alkynyl groups (e.g., substituted and unsubstituted $C_2-C_{20}$ alkynyl groups); substituted and unsubstituted aryl groups (e.g., substituted and unsubstituted phenyl, naphthyl, fluorenyl, anthracenyl and phenanthracenyl); and substituted and unsubstituted heteroaryl groups (e.g., substituted and unsubstituted pyridyl, quinolinyl, isoquinolinyl, bipyridyl, pyridazinyl, cinnolinyl, phthalazinyl, pyrimidinyl, quinazolinyl, pyrazinyl, quinoxalinyl, phenanthrolinyl, triazinyl, pyrrolyl, indolyl, furfuryl, benzofurfuryl, thienyl, benzothienyl, pyrazolyl, indazolyl, imidazolyl, benzimidazolyl, triazolyl, benzotriazolyl, tetrazolyl, oxazolyl, benzoxazolyl, isoxazolyl, benzisoxazolyl, thiazolyl, benzothiazolyl, isothiazolyl, benzisothiazolyl, thiadiazolyl, benzothiadiazolyl, thiatriazolyl, purinyl, carbazolyl and azaindolyl).

The indeno-fused naphthopyrans of the present invention are also free of a fused group, such as a fused ring group (e.g., 5 membered carbocyclic groups or a 5 membered heterocyclic groups having a heteroatom selected from oxygen, sulfur or nitrogen), formed between the 11-position and the 10-position and/or the 12-position of the indeno-fused naphthopyran.

The indeno-fused naphthopyrans of the present invention are free of halo-substituted groups bonded to the 11-position thereof. As used herein, the term halo-substituted group (and related terms, such as haloalkyl groups, haloalkenyl groups, haloalkynyl groups, haloaryl groups and halo-heteroaryl groups) means a group in which at least one, and less than all of the available hydrogen groups thereof is substituted with a halo group. For example, halomethyl groups include, $—CH_2X$ and $—CHX_2$; and perhalophenyl groups include, $C_6H_4X$, $C_6H_3X_2$, $C_6H_2X_3$ and $C_6HX_4$, where X represents one or more halo groups (e.g., F).

The indeno-fused naphthopyrans of the present invention are free of perhalo-substituted groups bonded to the 11-position thereof. As used herein, the term perhalo-substituted group (and related terms, such as perhaloalkyl groups, perhaloalkenyl groups, perhaloalkynyl groups, perhaloaryl groups and perhalo-heteroaryl groups) means a group in which all of the available hydrogen groups thereof is substituted with a halo group. For example, perhalomethyl is $—CX_3$; perhalophenyl is $C_6X_5$, where X represents one or more halo groups (e.g., F).

The photochromic material of the present invention has an amino group bonded to the 6-position of the indeno-fused naphthopyran thereof. In particular, an amine-nitrogen (and in particular one or a single amine-nitrogen) of the amino group is bonded to the 6-position of the indeno-fused naphthopyran. The amino group is selected from secondary amines and tertiary amines.

The amino group bonded to the 6-position of said indeno-fused naphthopyran may be selected from:
(1) $—N(R_{15})R_{16}$ in which $R_{15}$ and $R_{16}$ are each selected from hydrogen (provided that only one of $R_{15}$ and $R_{16}$ is hydrogen), $C_1-C_{12}$ alkyl, phenyl, naphthyl, heteroaromatic groups, furanyl, benzofuran-2-yl, benzofuran-3-yl, thienyl, benzothien-2-yl, benzothien-3-yl, dibenzofuranyl, dibenzothienyl, benzopyridyl and fluorenyl, $C_1-C_{12}$ alkylaryl, $C_3-C_{20}$ cycloalkyl, $C_4-C_{20}$ bicycloalkyl, $C_5-C_{20}$ tricycloalkyl and $C_1-C_{20}$ alkoxyalkyl, wherein the aryl group is phenyl or naphthyl (e.g., $C_4-C_{12}$ alkylphenyl or $C_1-C_{12}$ alkylnaphthyl);
(2) a nitrogen containing ring represented by the following general graphic Formula-(III), $C_3-C_{20}$ cycloalkyl, $C_4-C_{20}$ bicycloalkyl, $C_5-C_{20}$ tricycloalkyl and $C_1-C_{20}$ alkoxyalkyl, wherein the aryl group is phenyl or naphthyl (e.g., $C_1-C_{12}$ alkylphenyl or $C_1-C_{12}$ alkylnaphthyl);
(2) a nitrogen containing ring represented by the following general graphic Formula-(III),

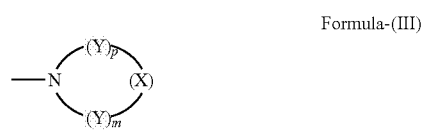

Formula-(III)

in which Y is independently selected for each p and each m from $—CH_2—$, $—CH(R_{17})—$, $—C(R_{17})(R_{17})—$, $—CH(aryl)-$, $—C(aryl)_2-$, and $—C(R_{17})(aryl)-$, and X is selected from $—Y—$, $—O—$, $—S—$, $—S(O)—$, $—S(O_2)—$, $—NH—$, $—NR_{17}—$ and $—N$-aryl, wherein $R_{17}$ is in each instance independently selected from $C_1-C_{12}$ alkyl, said aryl substituent is phenyl or naphthyl, m is an integer selected from 1, 2 or 3, and p is the integer selected from 0, 1, 2, or 3, provided that when p is 0, X is Y; and (3) a group represented by the following graphic Formulae-(IV) and -(V):

Formula-(IV)

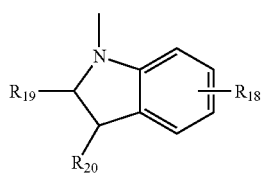

Formula-(V)

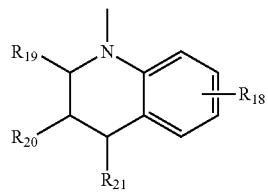

in which $R_{19}$, $R_{20}$ and $R_{21}$ are each hydrogen, $C_1$-$C_{12}$ alkyl, phenyl or naphthyl, or the groups $R_{19}$ and $R_{20}$ together form a ring of 5 to 8 carbon atoms, and $R_{18}$ is $C_1$-$C_{12}$ alkyl, $C_1$-$C_{12}$ alkoxy, fluoro or chloro.

In a particular embodiment of the present invention, the amino group bonded to the 6-position of the indeno-fused naphthopyran is represented by the following general Formulas-(VI) and -(VII).

Formula-(VI)

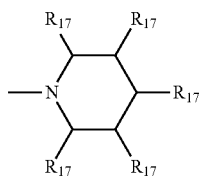

Formula-(VII)

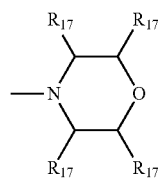

In the case of Formulas-(VI) and -(VII), $R_{17}$ is in each instance independently selected from hydrogen or $C_1$-$C_{12}$ alkyl, and correspondingly, the amino group bonded to the 6-position of the indeno-fused naphthopyran is selected from substituted or unsubstituted piperidenyl (e.g., Formula-VI), and substituted or unsubstituted morpholinyl (e.g., Formula-VII). In a particular embodiment, the amino group bonded to the 6-position of the indeno-fused naphthopyran is selected from substituted and unsubstituted piperidenyl (e.g., Formula-VI).

The amino group bonded to the 6-position of the indeno-fused naphthopyran may, in an embodiment, include a reactive substituent or a compatibilizing substituent. In a particular embodiment of the present invention, the amino group bonded to the 6-position of the indeno-fused naphthopyran is free of a reactive substituent. In a further particular embodiment of the present invention, the amino group bonded to the 6-position of the indeno-fused naphthopyran is: free of one or more reactive substituents; and free of one or more compatibilizing substituents.

As used herein the term "reactive substituent" means an arrangement of atoms, wherein a portion of the arrangement comprises a reactive moiety or a residue thereof. As used herein, the term "moiety" means a part or portion of an organic molecule that has a characteristic chemical property. As used herein, the term "reactive moiety" means a part or portion of an organic molecule that may react to form one or more bond(s) with an intermediate in a polymerization reaction, or with a polymer into which it has been incorporated. As used herein the term "intermediate in a polymerization reaction" means any combination of two or more monomer units that are capable of reacting to form one or more bond(s) to additional monomer unit(s) to continue a polymerization reaction or, alternatively, reacting with a reactive moiety of the reactive substituent on the photochromic material. For example, although not limiting herein, the reactive moiety may react with an intermediate in a polymerization reaction of a monomer or oligomer as a co-monomer in the polymerization reaction or may react as, for example and without limitation, a nucleophile or electrophile, that adds (or is incorporated) into the intermediate. Alternatively, the reactive moiety may react with a group (such as, but not limited to a hydroxyl group) on a polymer (e.g., a group on a polymer backbone, or a group pendent from a polymer backbone).

As used herein the term "residue of a reactive moiety" means that which remains after a reactive moiety has been reacted with a protecting group or an intermediate in a polymerization reaction. As used herein the term "protecting group" means a group that is removably bonded to a reactive moiety that prevents the reactive moiety from participating in a reaction until the group is removed. Optionally, the reactive substituents according to various non-limiting embodiments disclosed herein may further comprise a linking group. As used herein the term "linking group" means one or more group(s) or chain(s) of atoms that connect the reactive moiety to the photochromic material.

Some substituents may be both compatiblizing and reactive. For example, a substituent that comprises hydrophilic linking group(s) that connects a reactive moiety to the photochromic material may be both a reactive substituent and a compatiblizing substituent. As used herein, such substituents may be termed as either a reactive substituent or a compatiblizing substituent. Examples of reactive substituents and compatiblizing substituents that may be bonded to the amino group bonded to the 6-position of the indeno-fused naphthopyran, include those as described further herein with regard to Formulas-(XIII) through -(XXI) (e.g., formulas -A'-D-E-G-J through -A'-J).

The 13-position of the indeno-fused naphthopyran of the present invention is free of spiro-substituents (i.e., free of spiro-cyclic groups). The 13-position of the indeno-fused naphthopyran being "free of spiro-substituents" means that if the 13-position of the indeno-fused naphthopyran is di-substituted, the substituent groups do not together form a spiro group (i.e., a spiro-cyclic group). As used herein the phrase "free of spiro-cyclic groups at the 13-position" means that if the 13-position of the indeno-fused naphthopyran is di-substituted, the substituent groups do not together form a spiro-cyclic group. Non-limiting examples of suitable groups that may be bonded at the 13-position of the indeno-fused naphthopyran are described in further detail herein with regard to $R^{13}$ and $R^{14}$.

In an embodiment of the present invention, the 13-position of the indeno-fused naphthopyran is free of: halo-substituted groups (e.g., haloalkyl groups, haloalkenyl groups, haloalkynyl groups, haloaryl groups and halo-heteroaryl groups); and/or perhalo-substituted groups (e.g., perhaloalkyl groups, perhaloalkenyl groups, perhaloalkynyl groups, perhaloaryl groups and perhalo-heteroaryl groups) bonded thereto. The terms halo-substituted groups and perhalo-substituted groups are as defined previously herein with regard to the 11-position.

The present invention also relates, more particularly and graphically, to a photochromic material that includes an indeno-fused naphthopyran that is selected from: an indeno [2',3':3,4]naphtho[1,2-b]pyran, represented by general Formula-(I); and/or an indeno[1',2':4,3]naphtho[2,1-b]pyran represented by general Formula-(II), as discussed previously herein. In a particular embodiment, the photochromic material is selected from an indeno[2',3':3,4]naphtho[1,2-b]pyran, represented by general Formula-(I),

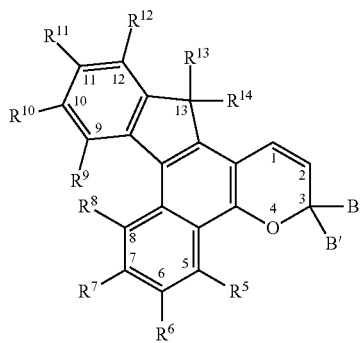

Formula-(I)

In Formula-(I), $R^{11}$ represents a halo group (e.g., fluoro) bonded to (i.e., bonded directly to) the 11-position of the indeno-fused naphthopyran, as discussed previously herein. In Formula-(I), $R^6$ represents the amino group bonded to the 6-position of the indeno-fused naphthopyran, in which an amine-nitrogen of the amino group is bonded to the 6-position, as discussed previously herein. The amino group is selected from secondary amines and tertiary amines.

With further reference to Formula-(I), $R^5$, $R^7$, $R^8$, $R^9$, $R^{10}$ and $R^{12}$ are each independently chosen in each case from: a reactive substituent; a compatiblizing substituent; hydrogen; $C_1$-$C_{12}$ alkyl; chloro; fluoro; $C_3$-$C_7$ cycloalkyl; a substituted or unsubstituted phenyl, said phenyl substituents being $C_1$-$C_{12}$ alkyl or $C_1$-$C_{12}$ alkoxy; —$OR_{10}'$ or —$OC(=O)R_{10}'$ wherein $R_{10}'$ is —S, hydrogen, amine, $C_1$-$C_{12}$ alkyl, phenyl $(C_1$-$C_3)$alkyl, mono$(C_1$-$C_6)$alkyl substituted phenyl$(C_1$-$C_3)$ alkyl, mono$(C_1$-$C_{12})$alkoxy substituted phenyl$(C_1$-$C_3)$alkyl, $(C_1$-$C_{12})$alkoxy$(C_1$-$C_{12})$alkyl, $C_3$-$C_7$ cycloalkyl or mono$(C_1$-$C_{12})$alkyl substituted $C_3$-$C_7$ cycloalkyl; —$N(R_{11}')R_{12}'$, wherein $R_{11}'$ and $R_{12}'$ are each independently hydrogen, $C_1$-$C_{12}$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl and fluorenyl, $C_1$-$C_{12}$alkylaryl, $C_3$-$C_{20}$ cycloalkyl, $C_4$-$C_{20}$ bicycloalkyl, $C_5$-$C_{20}$ tricycloalkyl or $C_1$-$C_{20}$ alkoxyalkyl, or $R_{11}'$ and $R_{12}'$ come together with the nitrogen atom to form a $C_3$-$C_{20}$ hetero-bicycloalkyl ring or a $C_4$-$C_{20}$ hetero-tricycloalkyl ring.

In addition, $R^5$, $R^7$, $R^8$, $R^9$, $R^{10}$ and $R^{12}$ may each independently chosen in each case from a nitrogen containing ring represented by the following Formula-(VIII),

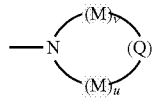

Formula-(VIII)

wherein each -M- is independently chosen for each occurrence from —$CH_2$—, —$CH(R_{13}')$—, —$C(R_{13}')_2$—, —$CH$(aryl)-, —$C(aryl)_2$- and —$C(R_{13}')$(aryl)-, and -Q- is -M-, —O—, —S—, —S(O)—, —$SO_2$—, —NH—, —$N(R_{13}')$— or —N(aryl)-, wherein each $R_{13}'$ is independently $C_1$-$C_{12}$ alkyl, each (aryl) is independently phenyl or naphthyl, u ranges from 1 to 3, and v ranges from 0 to 3, provided that if v is 0, -Q- is -M-; a group represented by:

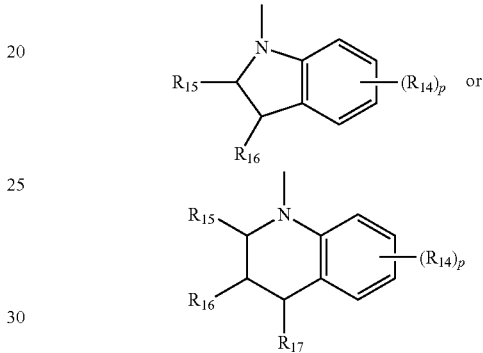

wherein each $R_{15}$, $R_{16}$ and $R_{17}$ is independently hydrogen, $C_1$-$C_{12}$ alkyl, phenyl or naphthyl, or $R_{15}$ and $R_{16}$ together form a ring of 5 to 8 carbon atoms, each $R_{14}$ is independently $C_1$-$C_{12}$ alkyl, $C_1$-$C_{12}$ alkoxy, fluoro or chloro, and p ranges from 0 to 3; and a substituted or unsubstituted $C_4$-$C_{18}$ spirobicyclic amine or a substituted or unsubstituted $C_4$-$C_{18}$ spirotricyclic amine, wherein the substituents are independently aryl, $C_1$-$C_{12}$ alkyl, $C_1$-$C_{12}$ alkoxy or phenyl$(C_1$-$C_{12})$alkyl.

With further reference to Formula-(I), $R^{13}$ and $R^{14}$ may each be independently chosen in each case from: a reactive substituent; a compatiblizing substituent; hydrogen; hydroxy; $C_1$-$C_{12}$ alkyl; $C_3$-$C_7$ cycloalkyl; allyl; a substituted or unsubstituted phenyl or benzyl, wherein each of said phenyl and benzyl substituents is independently $C_1$-$C_{12}$ alkyl or $C_1$-$C_{12}$ alkoxy; chloro; fluoro; a substituted or unsubstituted amino; —$C(O)R_9'$ wherein $R_9'$ is hydrogen, hydroxy, $C_1$-$C_{12}$ alkyl, $C_1$-$C_{12}$ alkoxy, an unsubstituted, mono- or di-substituted phenyl or naphthyl wherein each of said substituents is independently $C_1$-$C_{12}$ alkyl or $C_1$-$C_{12}$ alkoxy, phenoxy, mono- or di-$(C_1$-$C_{12})$alkyl substituted phenoxy, mono- or di-$(C_1$-$C_6)$alkoxy substituted phenoxy, amino, mono- or di-$(C_1$-$C_{12})$alkylamino, phenylamino, mono- or di-$(C_1$-$C_{12})$ alkyl substituted phenylamino or mono- or di-$(C_1$-$C_{12})$ alkoxy substituted phenylamino; and —$OR^{18}$ wherein $R^{18}$ is $C_1$-$C_{12}$ alkyl, phenyl$(C_1$-$C_{12})$alkyl, mono$(C_1$-$C_{12})$alkyl substituted phenyl$(C_1$-$C_{12})$alkyl, mono$(C_1$-$C_{12})$alkoxy substituted phenyl$(C_1$-$C_{12})$alkyl, $C_1$-$C_{12}$ alkoxy$(C_1$-$C_{12})$alkyl, $C_3$-$C_7$ cycloalkyl, mono$(C_1$-$C_4)$alkyl substituted $C_3$-$C_7$ cycloalkyl, $C_1$-$C_{12}$ chloroalkyl, $C_1$-$C_{12}$ fluoroalkyl, allyl or —$CH(R^{19})T$ wherein $R^{19}$ is hydrogen or $C_1$-$C_3$ alkyl, T is CN, $CF_3$ or $COOR^{20}$ wherein $R^{20}$ is hydrogen or $C_1$-$C_3$ alkyl, or wherein $R^{18}$ is —$C(=O)U$ wherein U is hydrogen, $C_1$-$C_{12}$ alkyl, $C_1$-$C_{12}$ alkoxy, an unsubstituted, mono- or di-substituted phenyl or naphthyl, wherein each of said substituents are independently $C_1$-$C_{12}$ alkyl or $C_1$-$C_{12}$ alkoxy, phenoxy, mono- or di-($C_1$-$C_{12}$)alkyl substituted phenoxy, mono- or di-($C_1$-$C_{12}$)alkoxy substituted phenoxy, amino, mono- or di-($C_1$-$C_{12}$)alkylamino, phenylamino, mono- or di-($C_1$-$C_{12}$) alkyl substituted phenylamino or mono- or di-($C_1$-$C_{12}$) alkoxy substituted phenylamino. In an embodiment, $R^{13}$ and $R^{14}$ may alternatively together form an oxo group.

With the photochromic material represented by Formula-(I), (II) and or (II'), B and B' may each independently be chosen in each case from: an aryl group that is mono-substituted with a reactive substituent or a compatiblizing substituent; an unsubstituted, mono-, di- or tri-substituted aryl group; 9-julolidinyl; an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl and fluorenyl.

The substituents of the aryl and heteroaromatic groups (from which B and/or B' may each be independently selected) are typically each independently selected from: hydroxy, aryl, mono- or di-($C_1$-$C_{12}$)alkoxyaryl, mono- or di-($C_1$-$C_{12}$) alkylaryl, haloaryl, $C_3$-$C_7$ cycloalkylaryl, $C_3$-$C_7$ cycloalkyl, $C_3$-$C_7$ cycloalkyloxy, $C_3$-$C_7$ cycloalkyloxy($C_1$-$C_{12}$)alkyl, $C_3$-$C_7$ cycloalkyloxy($C_1$-$C_{12}$)alkoxy, aryl($C_1$-$C_{12}$)alkyl, aryl ($C_1$-$C_{12}$)alkoxy, aryloxy, aryloxy($C_1$-$C_{12}$)alkyl, aryloxy($C_1$-$C_{12}$)alkoxy, mono- or di-($C_1$-$C_{12}$)alkylaryl($C_1$-$C_{12}$)alkyl, mono- or di-($C_1$-$C_{12}$)alkoxyaryl($C_1$-$C_{12}$)alkyl, mono- or di-($C_1$-$C_{12}$)alkylaryl($C_1$-$C_{12}$)alkoxy, mono- or di-($C_1$-$C_{12}$) alkoxyaryl($C_1$-$C_{12}$)alkoxy, amino, mono- or di-($C_1$-$C_{12}$) alkylamino, diarylamino, piperazino, N—($C_1$-$C_{12}$) alkylpiperazino, N-arylpiperazino, aziridino, indolino, piperidino, morpholino, thiomorpholino, tetrahydroquinolino, tetrahydroisoquinolino, pyrrolidyl, $C_1$-$C_{12}$ alkyl, $C_1$-$C_{12}$ haloalkyl, $C_1$-$C_{12}$ alkoxy, mono($C_1$-$C_{12}$)alkoxy($C_1$-$C_{12}$) alkyl, acryloxy, methacryloxy, halogen, or —C(=O) $R^{21}$ wherein $R^{21}$ is —$OR^{22}$, —$N(R^{23})R^{24}$, piperidino or morpholino, wherein $R^{22}$ is allyl, $C_1$-$C_{12}$ alkyl, phenyl, mono($C_1$-$C_{12}$)alkyl substituted phenyl, mono($C_1$-$C_{12}$)alkoxy substituted phenyl, phenyl($C_1$-$C_3$)alkyl, mono($C_1$-$C_{12}$)alkyl substituted phenyl($C_1$-$C_3$)alkyl, mono($C_1$-$C_{12}$)alkoxy substituted phenyl($C_1$-$C_3$)alkyl, $C_1$-$C_{12}$ alkoxy($C_1$-$C_{12}$)alkyl or $C_1$-$C_{12}$ haloalkyl, and $R^{23}$ and $R^{24}$ are each independently $C_1$-$C_{12}$ alkyl, $C_5$-$C_7$ cycloalkyl or a substituted or unsubstituted phenyl, the phenyl substituents independently being $C_1$-$C_{12}$ alkyl or $C_1$-$C_{12}$ alkoxy.

The B and B' groups of Formula-(I) may also be selected from, an unsubstituted or mono-substituted group chosen from pyrazolyl, imidazolyl, pyrazolinyl, imidazolinyl, pyrrolinyl, phenothiazinyl, phenoxazinyl, phenazinyl and acridinyl, the substituents being $C_1$-$C_{12}$ alkyl, $C_1$-$C_{12}$ alkoxy, phenyl or halogen; and a mono-substituted phenyl, in which the phenyl has a substituent located at the para position thereof, the substituent being a dicarboxylic acid residue or derivative thereof, a diamine residue or derivative thereof, an amino alcohol residue or derivative thereof, a polyol residue or derivative thereof, —($CH_2$)—, —($CH_2$)$_t$— or —[O—($CH_2$)$_t$]$_k$—, wherein "t" may range form 2 to 6 and "k" may range from 1 to 50, wherein the substituent may be connected to an aryl group on another photochromic material.

The B and B' groups of Formula-(I) may also each independently be selected from a group represented by the following general formulas (XXXA) and/or (XXXB):

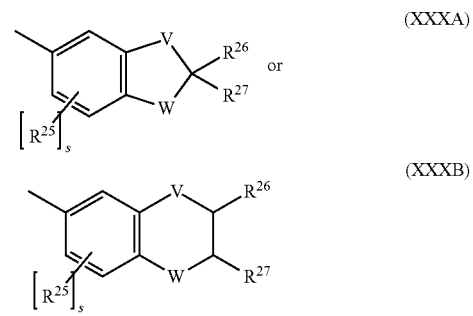

With reference to formulas (XXXA) and (XXXB) above, non-limiting examples of groups that V may represent according to various non-limiting embodiments disclosed herein include represent —$CH_2$— and —O—. Non-limiting examples of groups that W may represent according to various non-limiting embodiments disclosed herein include oxygen and substituted nitrogen, provided that if W is substituted nitrogen, V is —$CH_2$—. Suitable non-limiting examples of nitrogen substituents include hydrogen, $C_1$-$C_{12}$ alkyl and $C_1$-$C_{12}$ acyl. Further, according to various non-limiting embodiments disclosed herein, "s" may range from 0 to 2, and, if s is greater than one, each group represented by $R^{25}$ may be the same as or different from one or more other $R^{25}$ groups. Non-liming examples of groups that $R^{25}$ may represent include $C_1$-$C_{12}$ alkyl, $C_1$-$C_{12}$ alkoxy, hydroxy and halogen. Non-limiting examples of groups that $R^{26}$ and $R^{27}$ may represent according to various non-limiting embodiments disclosed herein include hydrogen and $C_1$-$C_{12}$ alkyl.

The B and B' groups of Formula-(I) may further each be independently selected from a group represented by the following general formula (XXXC):

With reference to (XXXC) above, non-limiting examples of groups that $R^{28}$ may represent according to various non-limiting embodiments disclosed herein include hydrogen and $C_1$-$C_{12}$ alkyl. Non-limiting examples of groups that $R^{29}$ may represent according to various non-limiting embodiments disclosed herein include an unsubstituted, mono- or di-substituted naphthyl, phenyl, furanyl or thienyl, said substituents being $C_1$-$C_{12}$ alkyl, $C_1$-$C_{12}$ alkoxy or halogen.

The B and B' groups of Formula-(I) taken together may form a fluoren-9-ylidene or mono- or di-substituted fluoren-9-ylidene. Each of the fluoren-9-ylidene substituents may independently be selected from $C_1$-$C_{12}$ alkyl, $C_1$-$C_{12}$ alkoxy or halogen.

With the indeno-fused naphthopyran represented by Formula-(I), $R^{13}$ and $R^{14}$ at the 13-position of said indeno-fused naphthopyran are in each case substantially free of spiro-substituents (i.e., free of spiro-cyclic groups). In particular, the $R^{13}$ and $R^{14}$ groups do not together form a spiro-cyclic group.

The amino group $R^6$ bonded to the 6-position of said indeno-fused naphthopyran is as described previously herein, and in particular may be selected from:

(1) —$N(R_{15})R_{16}$ in which $R_{15}$ and $R_{16}$ are each selected from hydrogen (provided that only one of $R_{15}$ and $R_{16}$ is hydrogen), $C_1$-$C_{12}$ alkyl, phenyl, naphthyl, heteroaromatic groups, furanyl, benzofuran-2-yl, benzofuran-3-yl, thienyl, benzothien-2-yl, benzothien-3-yl, dibenzofuranyl, dibenzothienyl, benzopyridyl and fluorenyl, $C_1$-$C_{12}$ alkylaryl, $C_3$-$C_{20}$ cycloalkyl, $C_4$-$C_{20}$ bicycloalkyl, $C_5$-$C_{20}$ tricycloalkyl and $C_1$-$C_{20}$ alkoxyalkyl, wherein the aryl group is phenyl or naphthyl (e.g., $C_1$-$C_{12}$ alkylphenyl or $C_1$-$C_{12}$ alkylnaphthyl);

(2) a nitrogen containing ring represented by the following general graphic Formula-(III),

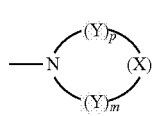

Formula-(III)

in which Y is independently selected for each p and each m from —$CH_2$—, —$CH(R_{17})$—, —$C(R_{17})(R_{17})$—, —CH(aryl)-, —$C(aryl)_2$-, and —$C(R_{17})(aryl)$-, and X is selected from —Y—, —O—, —S—, —S(O)—, —$S(O_2)$—, —NH—, —$NR_{17}$— and —N-aryl, wherein $R_{17}$ is in each instance independently selected from $C_1$-$C_{12}$ alkyl, said aryl substituent is phenyl or naphthyl, m is an integer selected from 1, 2 or 3, and p is the integer selected from 0, 1, 2, or 3, provided that when p is 0, X is Y; and (3) a group represented by the following graphic Formulae-(IV) and -(V):

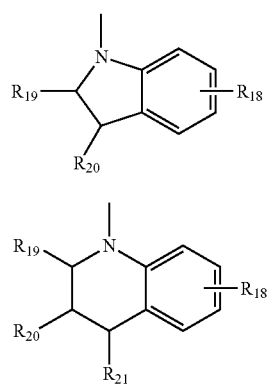

Formula-(IV)

Formula-(V)

in which $R_{19}$, $R_{20}$ and $R_{21}$ are each hydrogen, $C_1$-$C_{12}$ alkyl, phenyl or naphthyl, or the groups $R_{19}$ and $R_{20}$ together form a ring of 5 to 8 carbon atoms, and $R_{18}$ is $C_1$-$C_{12}$ alkyl, $C_1$-$C_{12}$ alkoxy, fluoro or chloro.

In a particular embodiment of the present invention, the amino group $R^6$ bonded to the 6-position of the indeno-fused naphthopyran is represented by the following general Formulas-(VI) and -(VII).

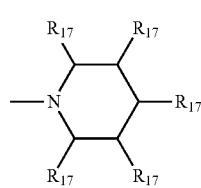

Formula-(VI)

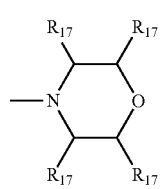

Formula-(VII)

In the case of Formulas-(VI) and -(VII), $R_{17}$ is in each instance independently selected from hydrogen or $C_1$-$C_{12}$ alkyl, and correspondingly, the amino group bonded to the 6-position of the indeno-fused naphthopyran is selected from substituted or unsubstituted piperidenyl (e.g., Formula-VI), and substituted or unsubstituted morpholinyl (e.g., Formula-VII). In a particular embodiment, the amino group bonded to the 6-position of the indeno-fused naphthopyran is selected from substituted and unsubstituted piperidenyl (e.g., Formula-VI).

The amino group $R^6$ bonded to the 6-position of the indeno-fused naphthopyran may, in an embodiment and as discussed previously herein, include a reactive substituent or a compatibilizing substituent. In a particular embodiment of the present invention, the amino group bonded to the 6-position of the indeno-fused naphthopyran is free of a reactive substituent. In a further particular embodiment of the present invention, the amino group $R^6$ bonded to the 6-position of the indeno-fused naphthopyran is: free of one or more reactive substituents; and free of one or more compatibilizing substituents.

The halo group $R^{11}$ bonded to the 11-position of the indeno-fused naphthopyran may be selected from fluoro (F), chloro (Cl), bromo (Br) or iodo (I). In an embodiment, the halo group $R^{11}$ bonded to the 11-position of the indeno-fused naphthopyran is selected from fluoro (F) or chloro (Cl). In a further embodiment, the halo group $R^{11}$ bonded to the 11-position of the indeno-fused naphthopyran is selected from fluoro (F).

As discussed previously herein, and as depicted in Formulas (I), (II), and (II'), the halo group $R^{11}$ is bonded (i.e., covalently bonded) directly to the 11-position of the indeno-fused naphthopyran, and the 11-position of the indeno-fused naphthopyran is free of a linking group (including divalent linking groups and higher/polyvalent linking groups) interposed between the 11-position and the halo group $R^{11}$. The halo group $R^{11}$ of the indeno-fused naphthopyran only represents a halo group, and does not include or represent any other group in the present invention. As discussed previously, the $R^{11}$ group of the indeno-fused naphthopyran of the present invention is also free of, does not include and does not represent a pi-conjugation extending group bonded to the 11-position. The $R^{11}$ group of the indeno-fused naphthopyran of the present invention does not form (or otherwise represent) a fused group, such as a fused ring group (e.g., 5 membered carbocyclic groups or a 5 membered heterocyclic groups having a heteroatom selected from oxygen, sulfur or nitrogen), with the $R^{10}$ and/or the $R^{12}$ groups of the indeno-fused naphthopyran.

The $R^{11}$ group of the indeno-fused naphthopyran of the present invention is free of and does not represent a halo-substituted group (e.g., haloalkenyl groups, haloalkynyl groups, haloaryl groups and halo-heteroaryl groups) or a per-halo-substituted groups (e.g., perhaloalkyl groups, perhaloalkenyl groups, perhaloalkynyl groups, perhaloaryl groups and perhalo-heteroaryl groups). The terms halo-substituted group and perhalo-substituted group are each as defined previously herein.

In a particular embodiment of the present invention, and with further reference to the indeno-fused naphthopyran represented by Formula-(I): $R^5$, $R^7$, $R^8$, $R^9$, $R^{10}$ and $R^{12}$ are each hydrogen; $R^{13}$ and $R^{14}$ are each independently selected from $C_1$-$C_6$ alkyl (e.g., methyl), and $C_3$-$C_7$ cycloalkyl (e.g., cyclopentyl and/or cyclohexyl); and B and B' are each independently selected from aryl substituted with $C_1$-$C_6$ alkoxy (e.g., —$C_6H_4$—$OCH_3$), and aryl substituted wit morpholino (e.g.,

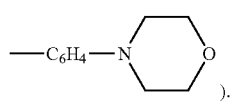
).

In a further embodiment, the indeno-fused naphthopyran of the photochromic material of the present invention may be selected from at least one of: 3,3-bis-(4-methoxyphenyl)-6-morpholino-11-fluoro-13,13-dimethyl-3H,13H-indeno[2,1-f]naphtho[1,2-b]pyran; 3-(4-methoxyphenyl-3-(4-(2-hydroxyethoxy)-phenyl)-6-morpholino-11-fluoro-13,13-dimethyl-3H,13H-indeno[2,1-f]naphtho[1,2-b]pyran; 3-(4-morpholinophenyl-3-phenyl)-6-morpholino-11-fluoro-13,13-dimethyl-3H,13H-indeno[2,1-f]naphtho[1,2-b]pyran; 3,3-bis-(4-methoxyphenyl)-6-piperidino-11-fluoro-13,13-dimethyl-3H,13H-indeno[2,1-f]naphtho[1,2-b]pyran; 3-(4-methoxyphenyl)-3-(4-(2-hydroxyethoxy)phenyl)-6-(3-methylmorpholino)-11-fluoro-13,13-dimethyl-3H,13H-indeno[2,1-f]naphtho[1,2-b]pyran.

For purposes of illustration, the indeno-fused naphthopyran, 3,3-bis-(4-methoxyphenyl)-6-morpholino-11-fluoro-13,13-dimethyl-3H,13H-indeno[2,1-f]naphtho[1,2-b]pyran, may be represented by the following general formula (A),

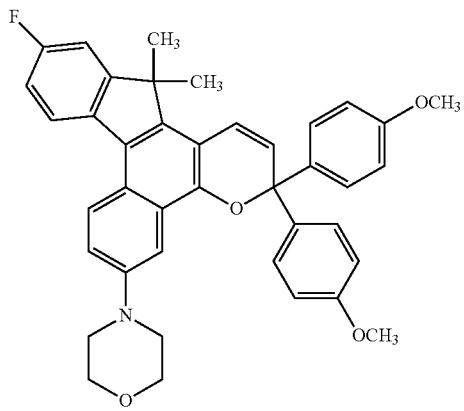

The indeno-fused naphthopyran, 3-(4-methoxyphenyl-3-(4-(2-hydroxyethoxy)-phenyl)-6-morpholine-11-fluoro-13,13-dimethyl-3H,13H-indeno[2,1-f]naphtho[1,2-b]pyran, may be represented by the following general formula (B),

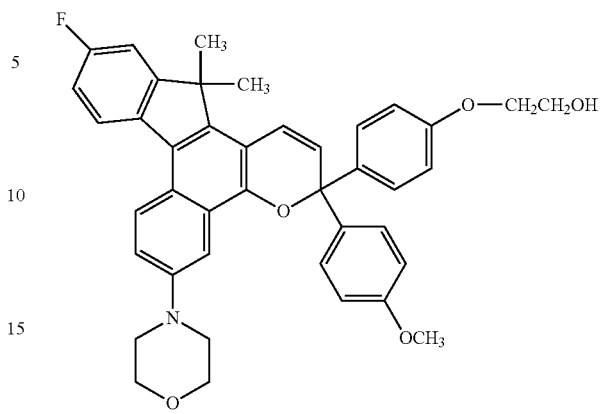

The indeno-fused naphthopyran, 3-(4-morpholinophenyl-3-phenyl)-6-morpholino-11-fluoro-13,13-dimethyl-3H, 13H-indeno[2,1-f]naphtho[1,2-b]pyran, may be represented by the following general formula (C),

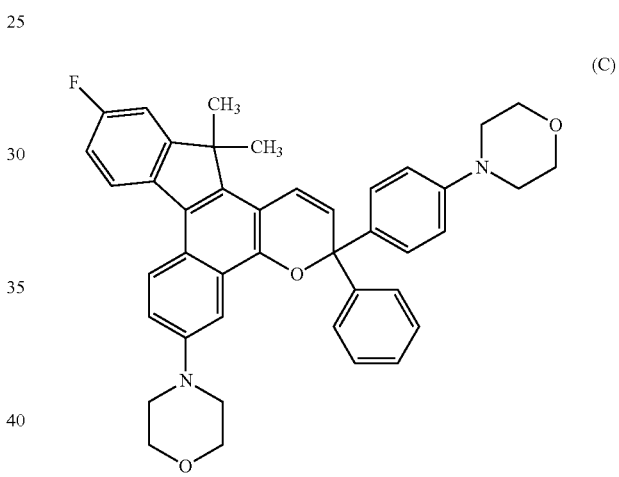

The indeno-fused naphthopyran, 3,3-bis-(4-methoxyphenyl)-6-piperidino-11-fluoro-13,13-dimethyl-3H,13H-indeno[2,1-f]naphtho[1,2-b]pyran, may be represented by the following general formula (D),

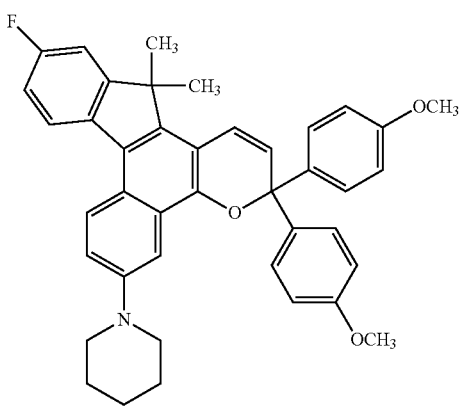

The indeno-fused naphthopyran, 3-(4-methoxyphenyl-3-(4-(2-hydroxyethoxy)phenyl)-6-(3-methylmorpholino)-11-fluoro-13,13-dimethyl-3H,13H-indeno[2,1-f]naphtho[1,2-b]pyran, may be represented by the following general formula (E),

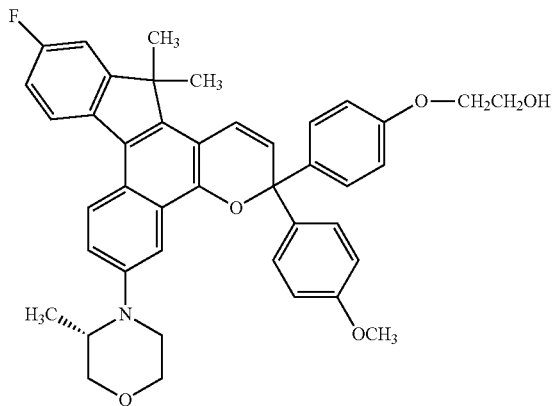

(E)

The amino group $R^6$ bonded to the 6-position of the indeno-fused naphthopyran may, in an embodiment, include at least one chiral carbon (e.g., one, two or three chiral carbons). In a particular embodiment, the amino group $R^6$ is a substituted cyclic amine represented by Formula-(III). In a further particular embodiment, the amino group $R^6$ is a substituted cyclic amine represented by Formula-(VI) (substituted piperidino) or Formula-(VII) (substituted morpholino) that contains at least one chiral carbon. The inclusion of a chiral carbon in the indeno-fused naphthopyrans of the present invention, allows for the possibility of resolving a racemic mixture thereof into its separate enantiomers by art-recognized methods (e.g., crystallization and/or chromatographic methods). Isolated enantiomers of the indeno-fused naphthopyrans of the present invention, may possess a combination of photochromic properties and plane-polarizing properties. The indeno-fused naphthopyran, 3-(4-methoxyphenyl)-3-(4-(2-hydroxyethoxy)phenyl)-6-(3-methylmorpholino)-11 fluoro-13,13-dimethyl-3H,13H-indeno[2,1-f] naphtho[1,2-b]pyran, has a chiral carbon morpholino group bonded to the 6-position thereof. See Formula (E).

As previously discussed, the photochromic materials according to present invention may include at least one of a reactive substituent and/or a compatiblizing substituent. Any one or more of the groups $R^5$ through $R^{10}$ and $R^{12}$ through $R^{14}$, and B and B' of the indeno-fused naphthopyran (e.g., represented by Formulas-I and/or -II) may include at least one of a reactive substituent and/or a compatiblizing substituent. If the photochromic material includes multiple reactive substituents and/or multiple compatiblizing substituents, each reactive substituent and each compatiblizing substituent may be independently chosen.

In an embodiment, the amino group ($R^6$) bonded to the 6-position of the indeno-fused naphthopyran is free of reactive substituents and compatiblizing substituents. Since the $R^{11}$ group bonded to the 11-position of the indeno-fused naphthopyran is, and may only be, a halo group, it too is free of reactive substituents and compatiblizing substituents. Accordingly, any one or more of the other groups of the indeno-fused naphthopyran (i.e., $R^5$, $R^7$, $R^8$, $R^9$, $R^{10}$, $R^{12}$, $R^{13}$, $R^{14}$, B and B') may include at least one reactive substituent and/or compatibilizing substituent. The reactive substituent and the compatibilizing substituent may each independently be represented in each case by one of:

| | | |
|---|---|---|
| -A'-D-E-G-J (XIII); | -G-E-G-J (XVI); | -D-E-G-J (XIX); |
| -A'-D-J (XIV); | -D-G-J (XVII); | -D-J (XX); |
| -A'-G-J (XV); | -G-J (XVIII); and | -A'-J (XXI). |

With reference to formulas (XIII) through (XXI) above, non-limiting examples of groups that -A'- may represent according to various non-limiting embodiments disclosed herein include —O—, —C(=O)—, —CH$_2$—, —OC(=O)— and —NHC(=O)—, provided that if -A'- represents —O—, -A'- forms at least one bond with -J.

Non-limiting examples of groups that -D- may represent according to various non-limiting embodiments include a diamine residue or a derivative thereof, wherein a first amino nitrogen of said diamine residue may form a bond with -A'-, or a substituent or an available position on the indeno-fused naphthopyran, and a second amino nitrogen of said diamine residue may form a bond with -E-, -G- or -J; and an amino alcohol residue or a derivative thereof, wherein an amino nitrogen of said amino alcohol residue may form a bond with -A'-, or a substituent or an available position on the indeno-fused naphthopyran, and an alcohol oxygen of said amino alcohol residue may form a bond with -E-, -G- or -J. Alternatively, according to various non-limiting embodiments disclosed herein the amino nitrogen of said amino alcohol residue may form a bond with -E-, -G- or -J, and said alcohol oxygen of said amino alcohol residue may form a bond with -A'-, or a substituent or an available position on the indeno-fused naphthopyran.

Non-limiting examples of suitable diamine residues that -D- may represent include an aliphatic diamine residue, a cyclo aliphatic diamine residue, a diazacycloalkane residue, an azacyclo aliphatic amine residue, a diazacrown ether residue, and an aromatic diamine residue. Specific non-limiting examples diamine residues that may be used in conjunction with various non-limiting embodiments disclosed herein include the following:

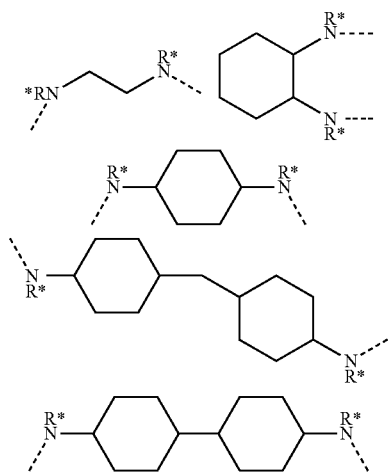

-continued

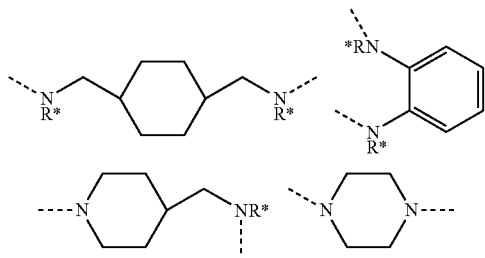

R* = H or alkyl

Non-limiting examples of suitable amino alcohol residues that -D- may represent include an aliphatic amino alcohol residue, a cyclo aliphatic amino alcohol residue, an azacyclo aliphatic alcohol residue, a diazacyclo aliphatic alcohol residue and an aromatic amino alcohol residue. Specific non-limiting examples amino alcohol residues that may be used in conjunction with various non-limiting embodiments disclosed herein include the following:

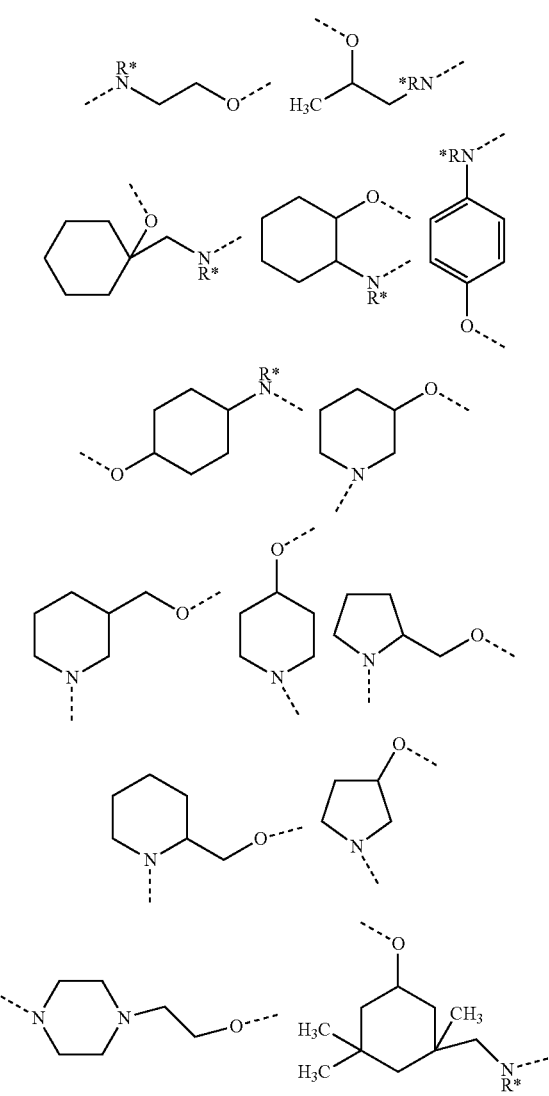

-continued

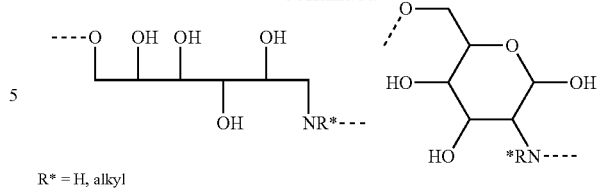

R* = H, alkyl

With continued reference to formulas (XIII) through (XXI) above, according to various non-limiting embodiments disclosed herein, -E- may represent a dicarboxylic acid residue or a derivative thereof, wherein a first carbonyl group of said dicarboxylic acid residue may form a bond with -G- or -D-, and a second carbonyl group of said dicarboxylic acid residue may form a bond with -G-. Non-limiting examples of suitable dicarboxylic acid residues that -E- may represent include an aliphatic dicarboxylic acid residue, a cycloaliphatic dicarboxylic acid residue and an aromatic dicarboxylic acid residue. Specific non-limiting examples of dicarboxylic acid residues that may be used in conjunction with various non-limiting embodiments disclosed herein include the following:

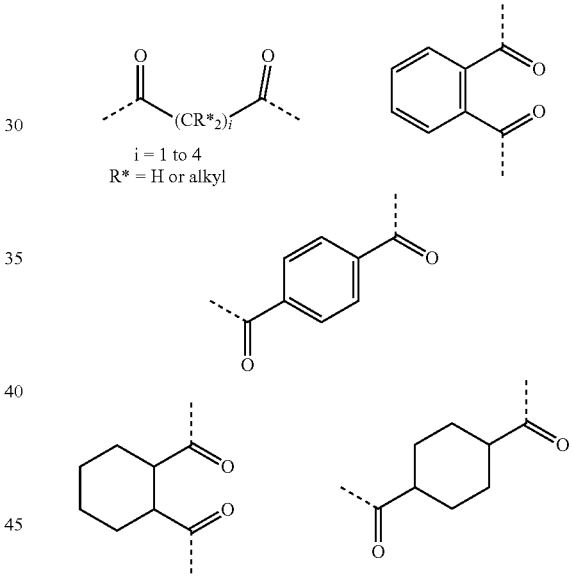

i = 1 to 4
R* = H or alkyl

According to various non-limiting embodiments disclosed herein, -G- may represent a group —[$(OC_2H_4)_x(OC_3H_6)_y(OC_4H_8)_z$]—O—, wherein x, y and z are each independently chosen and range from 0 to 50, and a sum of x, y, and z ranges from 1 to 50; a polyol residue or a derivative thereof, wherein a first polyol oxygen of said polyol residue may form a bond with -A'-, -D-, -E-, or a substituent or an available position on the indeno-fused naphthopyran, and a second polyol oxygen of said polyol may form a bond with -E- or -J; or a combination thereof, wherein the first polyol oxygen of the polyol residue forms a bond with a group —[$(OC_2H_4)_x(OC_3H_6)_y(OC_4H_8)_z$]— (i.e., to form the group —[$(OC_2H_4)_x(OC_3H_6)_y(OC_4H_8)_z$]—O—), and the second polyol oxygen forms a bond with -E- or -J. Non-limiting examples of suitable polyol residues that -G- may represent include an aliphatic polyol residue, a cyclo aliphatic polyol residue and an aromatic polyol residue.

Specific non-limiting examples of polyols from which the polyol residues that -G- may represent may be formed according to various non-limiting embodiments disclosed herein include (a) low molecular weight polyols having an average molecular weight less than 500, such as, but not limited to, those set forth in U.S. Pat. No. 6,555,028 at col. 4, lines 48-50, and col. 4, line 55 to col. 6, line 5, which disclosure is hereby specifically incorporated by reference herein; (b) polyester polyols, such as, but not limited to, those set forth in U.S. Pat. No. 6,555,028 at col. 5, lines 7-33, which disclosure is hereby specifically incorporated by reference herein; (c) polyether polyols, such as but not limited to those set forth in U.S. Pat. No. 6,555,028 at col. 5, lines 34-50, which disclosure is hereby specifically incorporated by reference herein; (d) amide-containing polyols, such as, but not limited to, those set forth in U.S. Pat. No. 6,555,028 at col. 5, lines 51-62, which disclosure is hereby specifically incorporated by reference; (e) epoxy polyols, such as, but not limited to, those set forth in U.S. Pat. No. 6,555,028 at col. 5 line 63 to col. 6, line 3, which disclosure is hereby specifically incorporated by reference herein; (f) polyhydric polyvinyl alcohols, such as, but not limited to, those set forth in U.S. Pat. No. 6,555,028 at col. 6, lines 4-12, which disclosure is hereby specifically incorporated by reference herein; (g) urethane polyols, such as, but not limited to those set forth in U.S. Pat. No. 6,555,028 at col. 6, lines 13-43, which disclosure is hereby specifically incorporated by reference herein; (h) polyacrylic polyols, such as, but not limited to those set forth in U.S. Pat. No. 6,555,028 at col. 6, lines 43 to col. 7, line 40, which disclosure is hereby specifically incorporated by reference herein; (i) polycarbonate polyols, such as, but not limited to, those set forth in U.S. Pat. No. 6,555,028 at col. 7, lines 41-55, which disclosure is hereby specifically incorporated by reference herein; and 6) mixtures of such polyols.

With further reference to formulas (XIII) through (XXI), according to various non-limiting embodiments disclosed herein, -J may represent a group —K, wherein —K represents a group such as, but not limited to, —CH$_2$COOH, —CH(CH$_3$)COOH, —C(O)(CH$_2$)$_w$COOH, —C$_6$H$_4$SO$_3$H, —C$_5$H$_{10}$SO$_3$H, —C$_4$H$_8$SO$_3$H, —C$_3$H$_6$SO$_3$H, —C$_2$H$_4$SO$_3$H and —SO$_3$H, wherein "w" ranges from 1 to 18. According to other non-limiting embodiments -J may represent hydrogen that forms a bond with an oxygen or a nitrogen of linking group to form a reactive moiety such as —OH or —NH. For example, according to various non-limiting embodiments disclosed herein, -J may represent hydrogen, provided that if -J represents hydrogen, -J is bonded to an oxygen of -D- or -G-, or a nitrogen of -D-.

According to still further non-limiting embodiments, -J may represent a group -L or residue thereof, wherein -L may represent a reactive moiety. For example, according to various non-limiting embodiments disclosed herein -L may represent a group such as, but not limited to, acryl, methacryl, crotyl, 2-(methacryloxy)ethylcarbamyl, 2-(methacryloxy)ethoxycarbonyl, 4-vinylphenyl, vinyl, 1-chlorovinyl or epoxy. As used herein, the terms acryl, methacryl, crotyl, 2-(methacryloxy)ethylcarbamyl, 2-(methacryloxy)ethoxycarbonyl, 4-vinylphenyl, vinyl, 1-chlorovinyl, and epoxy refer to the following structures:

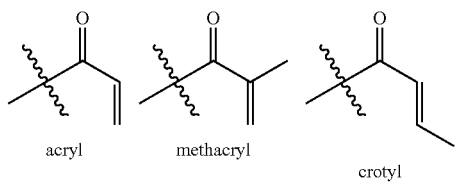

acryl   methacryl   crotyl

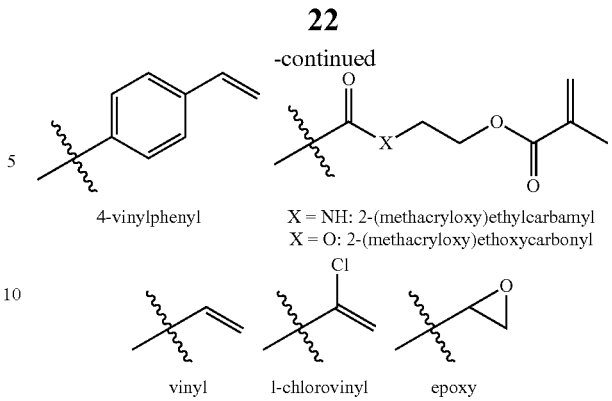

4-vinylphenyl

X = NH: 2-(methacryloxy)ethylcarbamyl
X = O: 2-(methacryloxy)ethoxycarbonyl vinyl   1-chlorovinyl   epoxy As previously discussed, -G- may represent a residue of a polyol, which is defined herein to include hydroxy-containing carbohydrates, such as those set forth in U.S. Pat. No. 6,555,028 at col. 7, line 56 to col. 8, line 17, which disclosure is hereby specifically incorporated by reference herein. The polyol residue may be formed, for example and without limitation herein, by the reaction of one or more of the polyol hydroxyl groups with a precursor of -A'-, such as a carboxylic acid or a methylene halide, a precursor of polyalkoxylated group, such as polyalkylene glycol, or a hydroxyl substituent of the indeno-fused naphthopyran. The polyol may be represented by q-(OH)$_a$ and the residue of the polyol may be represented by the formula —O-q-(OH)$_{n-1}$, wherein q is the backbone or main chain of the polyhydroxy compound and "a" is at least 2.

Further, as discussed above, one or more of the polyol oxygens of -G- may form a bond with -J (i.e., forming the group -G-J). For example, although not limiting herein, wherein the reactive and/or compatiblizing substituent comprises the group -G-J, if —O— represents a polyol residue and -J represents a group —K that contains a carboxyl terminating group, —O-J may be produced by reacting one or more polyol hydroxyl groups to form the group —K (for example as discussed with respect to Reactions B and C at col. 13, line 22 to col. 16, line 15 of U.S. Pat. No. 6,555,028, which disclosure is hereby specifically incorporated by reference herein) to produce a carboxylated polyol residue. Alternatively, if -J represents a group —K that contains a sulfo or sulfono terminating group, although not limiting herein, -G-J may be produced by acidic condensation of one or more of the polyol hydroxyl groups with HOC$_6$H$_4$SO$_3$H; HOC$_5$H$_{10}$SO$_3$H; HOC$_4$H$_8$SO$_3$H; HOC$_3$H$_6$SO$_3$H; HOC$_2$H$_4$SO$_3$H; or H$_2$SO$_4$, respectively. Further, although not limiting herein, if -G- represents a polyol residue and -J represents a group -L chosen from acryl, methacryl, 2-(methacryloxy)ethylcarbamyl and epoxy, -L may be added by condensation of the polyol residue with acryloyl chloride, methacryloyl chloride, 2-isocyanatoethyl methacrylate or epichlorohydrin, respectively.

Figure 2:
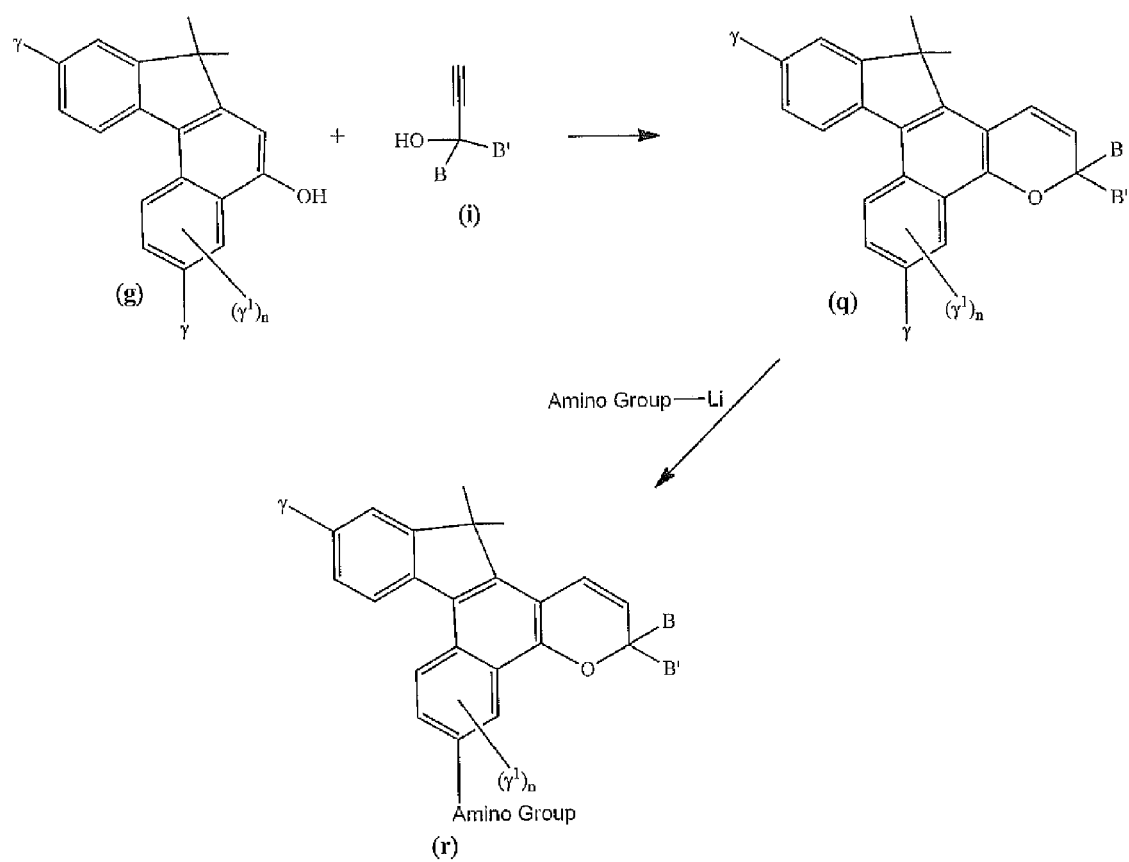
FIG. 2 is a representative schematic diagram of reaction scheme that may be used in making photochromic materials according to the present invention.

Methods of making photochromic materials that include the indeno-fused naphthopyrans according to the present invention are described here with reference to the general reaction schemes summarized and depicted in FIGS. 1 and 2 of the drawings. With reference to FIG. 1, there is depicted a reaction scheme for making substituted 7H-benzo[C]fluoren-5-ol compounds, that may be further reacted as shown in FIG. 2 to form photochromic materials comprising an indeno-fused naphthopyran according to the present invention. The reaction schemes depicted in FIGS. 1 and 2 are presented for purposes of illustration, and as such are not intended to be limiting with regard to the scope of the present invention.

With reference to FIG. 1, a solution of a γ-substituted benzoyl chloride, represented by structure (a) in FIG. 1, and γ-substituted benzene, represented by structure (b) in FIG. 1, which may have one or more substituents $\gamma^1$, in methylene chloride are added to a reaction flask. The γ-substituents are halo groups (e.g., fluoro), or are each a group that may be converted to or substituted with a halo group. Suitable $\gamma^1$ substituents include, for example and without limitation, those groups as described previously herein with regard to $R^5$, $R^6$, $R^7$ and $R^8$, depending on what position a particular $\gamma^1$ substituent is bonded to. Subscript n of FIGS. 1 and 2, relative to the moiety -$(\gamma^1)_n$, accordingly is from 0 to 3, inclusive of the recited values, and each $\gamma^1$ substituent is selected independently for each subscript n. Anhydrous aluminum chloride catalyzes the Friedel-Crafts acylation to give a substituted benzophenone represented by structure (c) in FIG. 1. This material is then reacted in a Stobbe reaction with dimethyl succinate to produce a mixture of half-esters, one of which is represented by structure (d) in FIG. 1. Thereafter the half-esters are reacted in acetic anhydride and toluene at an elevated temperature to produce, after recrystallization, a mixture of substituted naphthalene compounds, one of which is represented by structure (e) in FIG. 1. The mixture of substituted naphthalene compounds is then reacted with methyl magnesium chloride to produce a mixture of substituted naphthalene compounds, one of which is represented by structure (f) in FIG. 1. The mixture of substituted naphthalene compounds is then cyclized with dodecylbenzene sulfonic acid to afford a mixture of 7H-benzo[C]fluoren-5-ol compounds, one of which is represented by structure (g) in FIG. 1.

With reference to FIG. 2, the 7H-benzo[C]fluoren-5-ol compound represented by structure (g) may be reacted with a propargyl alcohol represented by structure (i) to produce the indeno-fused naphthopyran represented by structure (q). The γ-substituent at the 6-position of the indeno-fused naphthopyran represented by structure (q) is a halo group (e.g., fluoro). The compound represented by structure (q) is reacted with a lithium salt of an amino group described previously herein to form the indeno-fused naphthopyrans represented by structure (r) having an amino substituent at the 6-position. These compounds are indeno[2',3':3,4]naphtho[1,2-b]pyrans represented by the previously described general Formula I.

The indeno[1',2':4,3]naphtho[2,1-b]pyrans represented by general formula II may be prepared following the procedure described in U.S. Pat. No. 5,869,658 at column 4, line 38 to column 12, line 20, which disclosure is incorporated herein by reference, to prepare the base structure to which the substituents described herein above can be added.

The indeno[3',2':3,4]naphtho[1,2-b]pyran represented by general formula II' may be prepared following the procedure described in U.S. Pat. No. 6,736,998 at column 9, line 53 to column 18, line 35, which disclosure is incorporated herein by reference, to prepare the base structure to which the substituents described herein above can be added.

Further, non-limiting examples of methods of forming benzofurano-fused naphthopyrans, indolo-fused naphthopyrans, and/or benzothieno-fused naphthopyrans that may be useful (with appropriate modifications that will be recognized by skilled artisans) in forming the benzofurano-fused naphthopyrans, indolo-fused naphthopyrans and/or benzothieno-fused naphthopyrans according to various non-limiting embodiments disclosed herein are set forth in U.S. Pat. No. 5,651,923 at col. 6, line 43 to col. 13, line 48, which disclosure is hereby specifically incorporated by reference herein; International Patent Application Publication No. WO98/28289A1 at page 7, line 12 to page 9, line 10, which disclosure is hereby specifically incorporated by reference herein; and International Patent Application Publication No. WO99/23071A1 at page 9, lines 1 to page 14, line 3, which disclosure is hereby specifically incorporated by reference herein.

In an embodiment of the present invention, the photochromic material of the present invention, including the indeno-fused naphthopyrans as described, for example, with reference to Figures-(I), (II), and/or (II'), displays hyperchromic absorption of electromagnetic radiation having a wavelength from 320 nm to 440 nm, as compared to a comparative photochromic material comprising a comparable indeno-fused naphthopyran that is substantially free of: a halo group bonded to the 11-position thereof; and an amino group (e.g., as described with reference to $R^6$) bonded to the 6-position thereof. As used herein and in the claims, the term "hyperchromic absorption" refers to an increase in the absorption of electromagnetic radiation by (i) a photochromic material having a halo group bonded to the 11-position thereof, and an amino group (e.g., as described with reference to $R^6$) bonded to the 6-position of the indeno-fused naphthopyran, on a per molecule basis as compared to (ii) a comparable photochromic material that does not have a halo group bonded to the 11-position thereof, and an amino group bonded to the 6-position of the indeno-fused naphthopyran.

The present invention also relates to an optical element that includes one or more indeno-fused naphthopyrans according to the present invention. In particular, the optical element that includes one or more indeno-fused naphthopyrans that includes: an amino group bonded to the 6-position of said indeno-fused naphthopyran, the amine-nitrogen of said amino group being bonded to said 6-position, the amino group being selected from the group consisting of secondary amines and tertiary amines; and a halo group bonded to the 11-position of said indeno-fused naphthopyran. The 13-position of the indeno-fused naphthopyran, incorporated into the optical element, is substantially free of spiro-substituents. Optical elements that may include the photochromic materials, including the indeno-fused naphthopyrans, of the present invention are described in further detail herein below.

Optical elements including the photochromic materials, including the indeno-fused naphthopyrans, of the present invention, may be adapted for use behind a substrate that blocks a substantial portion of electromagnetic radiation in a range of 320 nm to 390 nm. At least a portion of the optical element absorbs at least a sufficient amount of electromagnetic radiation having a wavelength greater than 390 nm passing through the substrate that blocks a substantial portion of electromagnetic radiation in the range of 320 nm to 390 nm, such that at least a portion of the optical element transforms from a first state to a second state. The first state of the optical element is a bleached state (e.g., a substantially clear state), and the second state of the optical element is a colored state (e.g., a tinted state).

As discussed above, the photochromic materials according to the present invention may be incorporated into at least a portion of an organic material, such as a polymeric, oligomeric or monomeric material to form a photochromic composition, which may be used, for example and without limitation, to form photochromic articles, such as optical elements, and coating compositions that may be applied to various substrates. As used herein the terms "polymer" and "polymeric material" refer to homopolymers and copolymers (e.g., random copolymers, block copolymers, and alternating copolymers), as well as blends and other combinations thereof. As used herein the terms "oligomer" and "oligomeric material" refer to a combination of two or more monomer units that is capable of reacting with additional monomer unit(s). As used herein the term "incorporated into" means physically and/or chemically combined with. For example, the photochromic materials according to the present invention may be physically combined with at least a portion of an organic material, for example and without limitation, by mixing or imbibing the photochromic material into the organic material; and/or chemically combined with at least a portion of an organic material, for example and without limitation, by copolymerization or otherwise bonding the photochromic material to the organic material.

Further, the photochromic materials according to the present invention may each be used alone, in combination with other photochromic materials according to various non-limiting embodiments disclosed herein, or in combination with an appropriate complementary conventional photochromic material. For example, the photochromic materials according to the present invention may be used in conjunction with conventional photochromic materials having activated absorption maxima within the range of 300 to 1000 nanometers. Further, the photochromic materials according to the present invention may be used in conjunction with a complementary conventional polymerizable or a compatiblized photochromic material, such as for example, those disclosed in U.S. Pat. No. 6,113,814 (at col. 2, line 39 to col. 8, line 41), and U.S. Pat. No. 6,555,028 (at col. 2, line 65 to col. 12, line 56), which disclosures are hereby specifically incorporated by reference herein.

As discussed above, the photochromic compositions of the present invention may contain a mixture of photochromic materials. For example, although not limiting herein, mixtures of photochromic materials may be used to attain certain activated colors such as a near neutral gray or near neutral brown. See, for example, U.S. Pat. No. 5,645,767, col. 12, line 66 to col. 13, line 19, which describes the parameters that define neutral gray and brown colors and which disclosure is specifically incorporated by reference herein.

The present invention relates to a photochromic composition that includes an organic material, in which the organic material is a polymeric material, an oligomeric material and/or a monomeric material, and a photochromic material according to the present invention incorporated into at least a portion of the organic material. According to various non-limiting embodiments disclosed herein, the photochromic material may be incorporated into a portion of the organic material by at least one of blending and bonding the photochromic material with the organic material or a precursor thereof. As used herein with reference to the incorporation of photochromic materials into an organic material, the terms "blending" and "blended" mean that the photochromic material is intermixed or intermingled with the at least a portion of the organic material, but not bonded to the organic material. Further, as used herein with reference to the incorporation of photochromic materials into an organic material, the terms "bonding" or "bonded" mean that the photochromic material is linked to a portion of the organic material or a precursor thereof. For example, although not limiting herein, the photochromic material may be linked to the organic material through a reactive substituent.

According to a non-limiting embodiment wherein the organic material is a polymeric material, the photochromic material of the present invention may be incorporated into at least a portion of the polymeric material or at least a portion of the monomeric material or oligomeric material from which the polymeric material is formed. For example, photochromic materials according to various non-limiting embodiments disclosed herein that have a reactive substituent may be bonded to an organic material such as a monomer, oligomer, or polymer having a group with which a reactive moiety may be reacted, or the reactive moiety may be reacted as a co-monomer in the polymerization reaction from which the organic material is formed, for example, in a co-polymerization process.

As discussed above, the photochromic compositions according to various non-limiting embodiments disclosed herein may comprise an organic material chosen from a polymeric material, an oligomeric material and/or a monomeric material. Examples of polymeric materials that may be used in conjunction with various non-limiting embodiments disclosed herein include, without limitation: polymers of bis (allyl carbonate) monomers; diethylene glycol dimethacrylate monomers; diisopropenyl benzene monomers; ethoxylated bisphenol A dimethacrylate monomers; ethylene glycol bismethacrylate monomers; poly(ethylene glycol) bismethacrylate monomers; ethoxylated phenol bismethacrylate monomers; alkoxylated polyhydric alcohol acrylate monomers, such as ethoxylated trimethylol propane triacrylate monomers; urethane acrylate monomers; vinylbenzene monomers; and styrene. Other non-limiting examples of suitable polymeric materials include polymers of polyfunctional, e.g., mono-, di- or multi-functional, acrylate and/or methacrylate monomers; poly($C_1$-$C_{12}$ alkyl methacrylates), such as poly(methyl methacrylate); poly(oxyalkylene) dimethacrylate; poly(alkoxylated phenol methacrylates); cellulose acetate; cellulose triacetate; cellulose acetate propionate; cellulose acetate butyrate; poly(vinyl acetate); poly(vinyl alcohol); poly(vinyl chloride); poly(vinylidene chloride); polyurethanes; polythiourethanes; thermoplastic polycarbonates; polyesters; poly(ethylene terephthalate); polystyrene; poly(□-methylstyrene); copolymers of styrene and methyl methacrylate; copolymers of styrene and acrylonitrile; polyvinylbutyral; and polymers of diallylidene pentaerythritol, particularly copolymers with polyol (allyl carbonate) monomers, e.g., diethylene glycol bis(allyl carbonate), and acrylate monomers, e.g., ethyl acrylate, butyl acrylate. Also contemplated are copolymers of the aforementioned monomers, combinations, and blends of the aforementioned polymers and copolymers with other polymers, e.g., to form interpenetrating network products.

Further, according to various non-limiting embodiments wherein transparency of the photochromic composition is desired, the organic material may be a transparent polymeric material. For example, according to various non-limiting embodiments, the polymeric material may be an optically clear polymeric material prepared from a thermoplastic polycarbonate resin, such as the resin derived from bisphenol A and phosgene, which is sold under the trademark, LEXAN®; a polyester, such as the material sold under the trademark, MYLAR®; a poly(methyl methacrylate), such as the material sold under the trademark, PLEXIGLAS®; and polymerizates of a polyol(allyl carbonate) monomer, especially diethylene glycol bis(allyl carbonate), which monomer is sold under the trademark CR-39®; and polyurea-polyurethane (polyurea urethane) polymers, which are prepared, for example, by the reaction of a polyurethane oligomer and a diamine curing agent, a composition for one such polymer being sold under the trademark TRIVEX® by PPG Industries, Inc. Other non-limiting examples of suitable polymeric materials include polymerizates of copolymers of a polyol (allyl carbonate), e.g., diethylene glycol bis(allyl carbonate), with other copolymerizable monomeric materials, such as, but not limited to: copolymers with vinyl acetate, copolymers with a polyurethane having terminal diacrylate functionality, and copolymers with aliphatic urethanes, the terminal portion of which contain allyl or acrylyl functional groups. Still other suitable polymeric materials include, without limitation, poly(vinyl acetate), polyvinylbutyral, polyurethane, polythiourethanes, polymers chosen from diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers, cellulose acetate, cellulose propionate, cellulose butyrate, cellulose acetate butyrate, polystyrene and copolymers of styrene with methyl methacrylate, vinyl acetate and acrylonitrile. According to one non-limiting embodiment, the polymeric material may be an optical resins sold by PPG Industries, Inc. under the CR-designation, e.g., CR-307, CR-407, and CR-607.

According to a particular non-limiting embodiment, the organic material is a polymeric material chosen from poly (carbonate); copolymers of ethylene and vinyl acetate; copolymers of ethylene and vinyl alcohol; copolymers of ethylene, vinyl acetate, and vinyl alcohol (such as those that result from the partial saponification of copolymers of ethylene and vinyl acetate); cellulose acetate butyrate; poly(urethane); poly(acrylate); poly(methacrylate); epoxies; aminoplast functional polymers; poly(anhydride); poly(urea urethane); N-alkoxymethyl(meth)acrylamide functional polymers; poly(siloxane); poly(silane); and combinations and mixtures thereof.

As previously discussed, the photochromic materials according to the present invention may display hyperchromic absorption of electromagnetic radiation having a wavelength from 320 nm to 440 nm as compared to a photochromic materials comprising a comparable indeno-fused naphthopyrans without an amino group bonded to the 6-position and without a halo group bonded to the 11-position thereof. Accordingly, photochromic compositions comprising the photochromic materials according to the present invention may also display increased absorption of electromagnetic radiation having a wavelength from 320 nm to 440 nm as compared to a photochromic composition comprising a comparable indeno-fused naphthopyran without an amino group bonded to the 6-position and without a halo group bonded to the 11-position thereof.

Additionally, as previously discussed, since the photochromic materials according to the present invention may display hyperchromic properties as discussed above, it is contemplated that the amount or concentration of the photochromic material present in photochromic compositions according to the present invention may be reduced as compared to the amount or concentration of a conventional photochromic materials that is typically required to achieve a desired optical effect. Since it may be possible to use less of the photochromic materials according to the present invention, than conventional photochromic materials, while still achieving the desired optical effects, it is contemplated that the photochromic materials according to the present invention may be advantageously employed in applications in which it is necessary or desirable to limit the amount of photochromic material used.

Further, as previously discussed, the photochromic materials according to the present invention may have a closed-form absorption spectrum for electromagnetic radiation having a wavelength ranging from 320 nm to 440 nm that is bathochromically shifted as compared to a closed-form absorption spectrum for electromagnetic radiation having a wavelength ranging from 320 nm to 440 nm of a photochromic material comprising a comparable indeno-fused naphthopyran without an amino group bonded to the 6-position and without a halo group bonded to the 11-position thereof. Accordingly, photochromic compositions comprising the photochromic materials according to the present invention may also have an absorption spectrum for electromagnetic radiation having a wavelength ranging from 320 nm to 440 nm that is bathochromically shifted as compared to an absorption spectrum for electromagnetic radiation having a wavelength ranging from 320 nm to 440 nm of a photochromic composition comprising a comparable indeno-fused naphthopyran without an amino group bonded to the 6-position and without a halo group bonded to the 11-position thereof.

As previously discussed, the present invention further relates to photochromic articles, such as optical elements, that incorporate the photochromic materials and compositions according to the present invention. As used herein the term "optical" means pertaining to or associated with light and/or vision. The optical elements according to the present invention may include, without limitation, ophthalmic elements, display elements, windows, mirrors, and liquid crystal cell elements. As used herein the term "ophthalmic" means pertaining to or associated with the eye and vision. Non-limiting examples of ophthalmic elements include corrective and non-corrective lenses, including single vision or multi-vision lenses, which may be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, magnifying lenses, protective lenses, visors, goggles, as well as, lenses for optical instruments (for example, cameras and telescopes). As used herein the term "display" means the visible or machine-readable representation of information in words, numbers, symbols, designs or drawings. Non-limiting examples of display elements include screens, monitors, and security elements, such as security marks. As used herein the term "window" means an aperture adapted to permit the transmission of radiation therethrough. Non-limiting examples of windows include automotive and aircraft transparencies, windshields, filters, shutters, and optical switches. As used herein the term "mirror" means a surface that specularly reflects a large fraction of incident light. As used herein the term "liquid crystal cell" refers to a structure containing a liquid crystal material that is capable of being ordered. One non-limiting example of a liquid crystal cell element is a liquid crystal display.

Various non-limiting embodiments according to the present invention relate to photochromic articles, such as optical elements, comprising a substrate and a photochromic material according to the present invention connected to a portion of the substrate. As used herein, the term "connected to" means associated with, either directly or indirectly through another material or structure.

In accordance with various embodiments of the present invention, in which the substrate of the photochromic article includes a polymeric material, the photochromic material may be connected to at least a portion of the substrate by incorporating the photochromic material into at least a portion of the polymeric material of the substrate, or by incorporating the photochromic material into at least a portion of the oligomeric or monomeric material from which the substrate is formed. For example, according to one non-limiting embodiment, the photochromic material may be incorporated into the polymeric material of the substrate by the cast-in-place method or by imbibition. Imbibition and the cast-in-place method are discussed in further detail herein below.

In accordance with further non-limiting embodiments of the present invention, the photochromic material may be connected to at least a portion of the substrate of the photochromic article as part of at least partial coating that is connected to at least a portion of a substrate. According to this non-limiting embodiment, the substrate may be a polymeric substrate or an inorganic substrate (such as, but not limited to, a glass substrate). Further, the photochromic material may be incorporated into at least a portion of a coating composition prior to application of the coating composition to the substrate, or alternatively, a coating composition may be applied to the substrate, at least partially set, and thereafter the photochromic material may be imbibed into at least a portion of the coating. As used herein, the terms "set" and "setting" include, without limitation, curing, polymerizing, cross-linking, cooling, and drying.

The at least partial coating comprising the photochromic material may be connected to at least a portion of the substrate, for example, by applying a coating composition comprising the photochromic material to at least a portion of a surface of the substrate, and at least partially setting the coating composition. Additionally or alternatively, the at least partial coating comprising the photochromic material may be connected to the substrate, for example, through one or more additional at least partial coatings. For example, while not limiting herein, according to various non-limiting embodiments, an additional coating composition may be applied to a portion of the surface of the substrate, at least partially set, and thereafter the coating composition comprising the photochromic material may be applied over the additional coating and at least partially set. Non-limiting methods of applying coatings compositions to substrates are discussed herein below.

Non-limiting examples of additional coatings and films that may be used in conjunction with the photochromic articles according to the present invention, include: primer coatings and films; protective coatings and films, including transitional coatings and films and abrasion resistant coatings and films; anti-reflective coatings and films; conventional photochromic coating and films; and polarizing coatings and films; and combinations thereof. As used herein the term "protective coating or film" refers to coatings or films that can prevent wear or abrasion, provide a transition in properties from one coating or film to another, protect against the effects of polymerization reaction chemicals and/or protect against deterioration due to environmental conditions such as moisture, heat, ultraviolet light, oxygen, etc.

Non-limiting examples of primer coatings and films that may be used in conjunction with various non-limiting embodiments of the present invention disclosed herein include coatings and films comprising coupling agents, at least partial hydrolysates of coupling agents, and mixtures thereof. As used herein "coupling agent" means a material having a group capable of reacting, binding and/or associating with a group on a surface. Coupling agents according to various non-limiting embodiments disclosed herein may include organometallics such as silanes, titanates, zirconates, aluminates, zirconium aluminates, hydrolysates thereof and mixtures thereof. As used herein the phrase "at least partial hydrolysates of coupling agents" means that some to all of the hydrolyzable groups on the coupling agent are hydrolyzed. Other non-limiting examples of primer coatings that are suitable for use in conjunction with the various non-limiting embodiments disclosed herein include those primer coatings described U.S. Pat. No. 6,025,026 at col. 3, line 3 to col. 11, line 40 and U.S. Pat. No. 6,150,430 at col. 2, line 39 to col. 7, line 58, which disclosures are hereby specifically incorporated herein by reference.

As used herein, the term "transitional coating and film" means a coating or film that aids in creating a gradient in properties between two coatings or films, or a coating and a film. For example, although not limiting herein, a transitional coating may aid in creating a gradient in hardness between a relatively hard coating and a relatively soft coating. Non-limiting examples of transitional coatings include radiation-cured, acrylate-based thin films as described in U.S. Patent Application Publication 2003/0165686 at paragraphs 79-173, which are hereby specifically incorporated by reference herein.

As used herein the term "abrasion resistant coating and film" refers to a protective polymeric material that demonstrates a resistance to abrasion that is greater than a standard reference material, e.g., a polymer made of CR-39® monomer available from PPG Industries, Inc, as tested in a method comparable to ASTM F-735 Standard Test Method for Abrasion Resistance of Transparent Plastics and Coatings Using the Oscillating Sand Method. Non-limiting examples of abrasion resistant coatings include, for example, abrasion-resistant coatings comprising organosilanes, organosiloxanes, abrasion-resistant coatings based on inorganic materials such as silica, titania and/or zirconia, organic abrasion-resistant coatings of the type that are ultraviolet light curable, oxygen barrier-coatings, UV-shielding coatings, and combinations thereof.

Non-limiting examples of antireflective coatings and films include a monolayer, multilayer or film of metal oxides, metal fluorides, or other such materials, which may be deposited onto the articles disclosed herein (or onto films that are applied to the articles), for example, through vacuum deposition, sputtering, etc. Non-limiting examples of conventional photochromic coatings and films include, but are not limited to, coatings and films comprising conventional photochromic materials. Non-limiting examples of polarizing coatings and films include, but are not limited to, coatings and films comprising dichroic compounds that are known in the art.

As discussed above, in accordance with the present invention, an additional at least partial coating or film may be formed on the substrate prior to forming the coating comprising the photochromic material according to the present invention, on the substrate. For example, according to certain non-limiting embodiments a primer coating may be formed on the substrate prior to applying the coating composition comprising the photochromic material. Additionally or alternatively, the additional at least partial coating or film may be formed on the substrate after forming coating comprising the photochromic material according to various non-limiting embodiments disclosed herein on the substrate, for example, as an overcoating. For example, according to certain non-limiting embodiments, a transitional coating may be formed over the coating comprising the photochromic material, and an abrasion resistant coating may be formed over the transitional coating.

In accordance with the present invention, there is further provided an optical element adapted for use behind a substrate that blocks a substantial portion of electromagnetic radiation in the range of 320 nm to 390 nm, the optical element comprising a photochromic material comprising an indeno-fused naphthopyran having an amino group bonded to the 6-position and an optional halo group bonded to the 11-position thereof, connected to at least a portion of the optical element, wherein at least a portion of the optical element absorbs a sufficient amount of electromagnetic radiation having a wavelength greater than 390 nm passing through the substrate that blocks a substantial portion of electromagnetic radiation in the range of 320 nm to 390 nm such that, that portion of the optical element transforms from a first state to a second state. For example, according to this non-limiting embodiment, the first state may be a bleached state and the second state may be a colored state that corresponds to the colored state of the photochromic material(s) incorporated therein.

As previously discussed, many conventional photochromic materials require electromagnetic radiation having a wavelength ranging from 320 nm to 390 nm to cause the photochromic material to transform from a closed-form to an open-form (e.g., from a bleached state to a colored state). Therefore, conventional photochromic materials may not achieve a desirably (or sufficiently) fully-colored state when used in applications that are shielded from a substantial amount of electromagnetic radiation in the range of 320 nm to 390 nm. Further, as previously discussed, photochromic materials according to the present invention may display both hyperchromic and bathochromic properties. That is, the indeno-fused naphthopyrans having an amino group bonded to the 6-position and an optional halo group bonded to the 11-position thereof according to the present invention, may not only display hyperchromic absorption of electromagnetic radiation as discussed above, but may also have a closed-form absorption spectrum for electromagnetic radiation having a wavelength ranging from 320 nm to 440 nm that is bathochromically shifted as compared to a closed-form absorption spectrum for electromagnetic radiation having a wavelength ranging from 320 nm to 440 nm of a comparable indeno-fused naphthopyran without an amino group bonded to the 6-position and without a halo group bonded to the 11-position thereof. Accordingly, the photochromic materials according to the present invention may absorb a sufficient amount of electromagnetic radiation passing through a substrate that blocks a substantial portion of electromagnetic radiation having a wavelength ranging from 320 to 390 nm such that the photochromic material may transform from a closed-form to an open-form. That is, the amount of electromagnetic radiation having a wavelength of greater than 390 nm that is absorbed by the photochromic materials according to the present invention may be sufficient to permit the photochromic materials to transform from a closed-form to an open-form, thereby enabling their use behind a substrate (e.g., an automotive windshield) that blocks a substantial portion of electromagnetic radiation having a wavelength ranging from 320 nm to 390 nm.

Non-limiting methods of making photochromic compositions and photochromic articles, such as optical elements, according to the present invention are here discussed in further detail as follows. A non-limiting embodiment provides a method of making a photochromic composition, the method includes incorporating a photochromic material into at least a portion of an organic material. Non-limiting methods of incorporating photochromic materials into an organic material include, for example, mixing the photochromic material into a solution or melt of a polymeric, oligomeric, or monomeric material, and subsequently at least partially setting the polymeric, oligomeric, or monomeric material (with or without bonding the photochromic material to the organic material); and imbibing the photochromic material into the organic material (with or without bonding the photochromic material to the organic material).

Another non-limiting embodiment provides a method of making a photochromic article comprising connecting a photochromic material according to the present invention, to at least a portion a substrate. For example, if the substrate includes a polymeric material, the photochromic material may be connected to at least a portion of the substrate by at least one of the cast-in-place method and by imbibition. For example, in the cast-in-place method, the photochromic material may be mixed with a polymeric solution or melt, or other oligomeric and/or monomeric solution or mixture, which is subsequently cast into a mold having a desired shape and at least partially set to form the substrate. Optionally, according to this non-limiting embodiment, the photochromic material may be bonded to a portion of the polymeric material of the substrate, for example, by co-polymerization with a monomeric precursor thereof. In the imbibition method, the photochromic material may be diffused into the polymeric material of the substrate after it is formed, for example, by immersing a substrate in a solution containing the photochromic material, with or without heating. Thereafter, although not required, the photochromic material may be bonded with the polymeric material.

Other non-limiting embodiments according to the present invention provide a method of making an optical element that includes connecting a photochromic material to at least a portion of a substrate by at least one of in-mold casting, coating and lamination. For example, according to one non-limiting embodiment, wherein the substrate comprises a polymeric material, the photochromic material may be connected to at least a portion of a substrate by in-mold casting. According to this non-limiting embodiment, a coating composition comprising the photochromic material, which may be a liquid coating composition or a powder coating composition, is applied to the surface of a mold and at least partially set. Thereafter, a polymer solution or melt, or oligomeric or monomeric solution or mixture is cast over the coating and at least partially set. After setting, the coated substrate is removed from the mold. Non-limiting examples of powder coatings in which the photochromic materials according to various non-limiting embodiments disclosed herein may be employed are set forth in U.S. Pat. No. 6,068,797 at col. 7, line 50 to col. 19, line 42, which disclosure is hereby specifically incorporated by reference herein.

In accordance with a further non-limiting embodiment of the present invention, in which the substrate comprises a polymeric material or an inorganic material such as glass, the photochromic material may be connected to at least a portion of a substrate by coating. Non-limiting examples of suitable coating methods include spin coating, spray coating (e.g., using a liquid or powder coating), curtain coating, roll coating, spin and spray coating, over-molding, and combinations thereof. For example, according to one non-limiting embodiment, the photochromic material may be connected to the substrate by over-molding. According to this non-limiting embodiment, a coating composition comprising the photochromic material (which may be a liquid coating composition or a powder coating composition as previously discussed) may be applied to a mold and then the substrate may be placed into the mold such that the substrate contacts the coating causing it to spread over at least a portion of the surface of the substrate. Thereafter, the coating composition may be at least partially set and the coated substrate may be removed from the mold. Alternatively, over-molding may be done by placing the substrate into a mold such that an open region is defined between the substrate and the mold, and thereafter injecting a coating composition comprising the photochromic material into the open region. Thereafter, the coating composition may be at least partially set and the coated substrate may be removed from the mold.

Additionally or alternatively, a coating composition (with or without a photochromic material) may be applied to a substrate (for example, by any of the previously described methods), the coating composition may be at least partially set, and thereafter, a photochromic material may be imbibed (as previously discussed) into the partially set coating composition. The so imbibed and partially set coating composition, may there-after be fully set (e.g., fully cross-linked).

In accordance with a further non-limiting embodiment, in which the substrate comprises a polymeric material or an inorganic material such as glass, the photochromic material may be connected to at least a portion of a substrate by lamination. According to this non-limiting embodiment, a film comprising the photochromic material may be adhered or otherwise connected to a portion of the substrate, with or without an adhesive and/or the application of heat and pressure. Thereafter, if desired, a second substrate may be applied over the first substrate and the two substrates may be laminated together (i.e., by the application of heat and pressure) to form an element wherein the film comprising the photochromic material is interposed between the two substrates. Methods of forming films comprising a photochromic material may include for example and without limitation, combining a photochromic material with a polymeric solution or oligomeric solution or mixture, casting or extruding a film therefrom, and, if required, at least partially setting the film. Additionally or alternatively, a film may be formed (with or without a photochromic material) and imbibed with the photochromic material (as discussed above).

Still further non-limiting embodiments according to the present invention, relate to the use of various combinations of the forgoing methods to form photochromic articles according to the present invention. For example, and without limitation herein, according to one non-limiting embodiment, a photochromic material may be connected to substrate by incorporation into an organic material from which the substrate is formed (for example, using the cast-in-place method and/or imbibition), and thereafter a photochromic material (which may be the same or different from the aforementioned photochromic material) may be connected to a portion of the substrate using the in-mold casting, coating and/or lamination methods discussed above.

Further, photochromic compositions and articles according to the present invention may further include other art-recognized additives that aid or assist in the processing and/or performance of the composition or article. Non-limiting examples of such additives include photoinitiators, thermal initiators, polymerization inhibitors, solvents, light stabilizers (such as, but not limited to, ultraviolet light absorbers and light stabilizers, such as hindered amine light stabilizers (MALS)), heat stabilizers, mold release agents, rheology control agents, leveling agents (such as, but not limited to, surfactants), free radical scavengers, adhesion promoters (such as hexanediol diacrylate and coupling agents), and combinations and mixtures thereof.

The photochromic materials according to the present invention may be used in amounts (or ratios) such that the organic material or substrate into which the photochromic materials are incorporated or otherwise connected exhibits desired optical properties. For example, the amount and types of photochromic materials may be selected such that the organic material or substrate may be clear or colorless when the photochromic material is in the closed-form (i.e., in the bleached or unactivated state) and may exhibit a desired resultant color when the photochromic material is in the open-form (that is, when activated by actinic radiation). The precise amount of the photochromic material to be utilized in the various photochromic compositions and articles described herein is not critical provided that a sufficient amount is used to produce the desired effect. The particular amount of the photochromic material used may depend on a variety of art-recognized factors, such as but not limited to, the absorption characteristics of the photochromic material, the color and intensity of the color desired upon activation, and the method used to incorporate or connect the photochromic material to the substrate. Although not limiting herein, according to various non-limiting embodiments disclosed herein, the amount of the photochromic material that is incorporated into an organic material may range from 0.01 to 40 weight percent, based on the weight of the organic material.

The embodiments described herein are further illustrated by the following non-limiting examples.

EXAMPLES

Part 1 describes the preparation of Examples 1-6 and Comparative Example 1. Part 2 describes the testing of the photochromic properties of the Examples.

Part 1—Preparation of Examples 1-6 and Comparative Example 1

Example 1

Step 1

2-Phenoxyethanol (34.5 g) and acetyl chloride 19.5 g) were added to 200 ml of methylene chloride in a 500 mL flask. The mixture was stirred at ice bath temperature while triethyl amine (25 g) was added dropwise. On completion of the addition, the mixture was allowed to warm to about 23° C. and subsequently was poured into 1 liter of water. The organic layer was separated, washed twice with 100 mL portions of water, and the solvent removed on a rotary evaporator. The resulting product, 1-acetoxy-2-phenoxyethane, had crystallized in the flask. The solid was suction filtered, washed with two 50 mL portions of hexane and dried to yield 32 g of product that was used in the next step without further purification.

Step 2

The product of Step 1 was dissolved in 200 mL of methylene chloride in a reaction flask with stirring along with 42 g of anisoyl chloride. While maintaining the temperature at 15-20° C., tin (IV) chloride (130 g) was added via syringe over a one hour period. On completion of the addition, the mixture was stirred an additional hour at 20° C., then carefully poured into a large volume of ice. After the ice melted, the organic layer was separated, washed with water (2×100 mL) and the solvent was removed on a rotary evaporator. The product (4-methoxy-4'(2-acetoxyethoxy)benzophenone, was taken up in 200 mL of ethanol containing 15 g of dissolved sodium hydroxide and the mixture refluxed for one hour. The reaction mixture was cooled and poured into 500 mL of water. Sufficent HCl was added to result in a pH of 5 and the aqueous ethanol was extracted with two 100 mL portions of methylene chloride. The solvent was removed on a rotary evaporator to give an oil that crystallized upon the addition of methanol. The solid 4-methoxy-4'(2-hydroxyethoxy)benzophenone was suction filtered and dried to yield 65 g.

Step 3

The product from Step 2 (10.9 g, 0.04 mol) was added to a 250 mL flask containing 100 mL of dry DMF that had been previously saturated with acetylene. The reaction mixture was stirred and cooled in an ice bath while 0.12 moles of sodium acetylide (purchased as an 18 percent suspension in xylene light mineral oil from Aldrich) was added via pipet. Upon completion of the addition, the reaction was allowed to warm to about 23° C. over a period of one hour, and then poured into one liter of ice water. The product, 1-(4-(2-hydroxyethoxy)phenyl)-1-phenyl-2-propyn-1-ol, separated as a pasty solid. The product was washed with water, then taken up in 100 mL of chloroform and subsequently used without further purification.

Step 4

The product of Step 4 of Example 1 of U.S. Pat. No. 7,556,751, 3,9-difluoro-7,7-dimethyl-5-hydroxy-7,4-benzo[C]fluorine (5.0 g), the product of Step 3 above, 1-(4-methoxyphenyl)-1-(4-(2-hydroxyethoxy)-phenyl-2-propyn-1-ol (5.0 g, 1.0 equivalent) and methylene chloride (300 mL) were combined in a 3-necked 500 mL reaction flask. p-Toluenesulfonic acid (PTSA, 300 mg, 0.1 equivalents) was added. The resulting reaction mixture was stirred at room temperature for 3 hours and 0.5 g of 1-(4-methoxyphenyl)-1-(4-(2-hydroxyethoxy)-phenyl-2-propyn-1-ol was added. The reaction mixture was stirred at room temperature for 3 hours and 0.5 g of 1-(4-methoxyphenyl)-1-(4-(2-hydroxyethoxy)-phenyl-2-propyn-1-ol and 0.3 g of the PTSA was added and the resulting reaction mixture was stirred for about 64 hours at room temperature. The reaction mixture was washed with 400 mL of a 1:1 mixture of saturated aqueous NaHCO$_3$ and water. The recovered organic layer was dried over anhydrous sodium sulfate. The solvent was removed by rotary evaporation to yield a bluish solid. This material was purified by column chromatography (40% ethyl acetate in hexanes as the eluant). The fractions were analyzed by TLC and HPLC. The pure fractions were combined, rotovaped, and dried under vacuum to get 7.95 grams of bluish foam that was recrystallized from diethyl ether to obtain an off-white solid.

1H NMR spectrum showed the product to have a structure consistent with 3-(4-methoxyphenyl)-3-(4-(2-hydroxyethoxy)phenyl-6,11-difluoro-13,13-dimethyl-3H,13H-indeno[2',3':3,4]naphtho[1,2-b]pyran.

Step 5

Morpholine (2.42 grams, 4 eq.) was weighed into a 250 mL dry reaction flask. Dry tetrahydrofuran (dTHF, 100 mL) was added to the reaction flask and stirred under a nitrogen atmosphere at room temperature. n-Butyl lithium (2.5 M in hexanes, 12.5 mL) was added dropwise to the reaction mixture over a 10-minute period. The product of Step 4 (4.0 grams) was added in portions over a 5-minute period to the reaction mixture. The color of the reaction mixture turned to deep brown and then deep green. The resulting mixture was heated for 2 hours at 35-40° C. After cooling to room temperature, the reaction mixture was poured into 200 mL of 10% hydrochloric acid solution and extracted with two 200 mL portions of ethyl acetate. The recovered organic layers were combined, washed with saturated NaCl solution (1×300 mL) and dried over anhydrous sodium sulfate. The solvent (ethyl acetate) was removed by rotary evaporation to yield a greenish oil that foamed upon drying. This material was purified by column chromatography (30% acetone in hexanes as the starting eluant). The fractions were analyzed by TLC and HPLC. The pure fractions were combined, rotovaped, and dried under vacuum. The structures were confirmed by NMR and Mass Spectrometry analysis to be 3-(4-methoxyphenyl-3-(4-(2-hydroxyethoxy)phenyl)-6,11-bismorpholino-13,13-dimethyl-3H,13H-indeno[2,1-f]naphtho[1,2-b]pyran (1.65 g) and the desired product of this Example 3,3-(4-methoxyphenyl)-3-(4-(2-hydroxyethoxy)phenyl)-6-morpholino-11-fluoro-13,13-dimethyl-3H,13H-indeno[2,1-f]naphtho[1,2-b]pyran (1.07 g).

Example 2

3-Methylmorpholine (0.8 g) was dissolved in dry TI-IF (dTHF, 40 mL) in a 3-necked 250 mL flask under nitrogen. n-Butyl lithium (2.5 M, in hexanes, 3.7 mL) was added slowly to reaction mixture at room temperature under nitrogen. The resulting solution was stirred for 30 minutes at room temperature. 3-(4-Methoxyphenyl-3-(4-(2-hydroxyethoxy)phenyl)-6,11-difluoro-13,13-dimethyl-3H,13H-indeno[2',3':3,4]naphtho[1,2-b]pyran (1.5 g), the product of Example 1 was slowly added to the reaction mixture. The reaction mixture was stirred at room temperature under nitrogen for about 24 hours; saturated aqueous NH$_4$Cl (40 mL) solution was added and the resulting mixture was extracted with ethyl acetate three times (3×30 mL). The recovered organic layers were combined, dried over anhydrous MgSO$_4$, and concentrated under vacuum to provide product (2.1 g). The product was purified by column chromatography (using as the eluent, hexanes/ethyl acetate, 1/9, v/v) to yield a greenish solid (1.0 g) after drying. A 1H NMR spectrum showed the product to have a structure consistent with 3-(4-methoxyphenyl-3-(4-(2-hydroxyethoxy)phenyl)-6-(3-methylmorpholino)-11-fluoro-13,13-dimethyl-3H,13H-indeno[2,1-f]naphtho[1,2-b]pyran.

Example 3

Morpholine (0.53 grams, 1.10 eq.) was weighed into a 250 mL dry reaction flask. Dry tetrahydrofuran (100 mL) was added to the reaction flask and stirred under a nitrogen atmosphere at room temperature. n-Butyl lithium (2.5 M in hexanes, 2.42 mL) was added dropwise to the reaction mixture over a 5 minute period. 3,3-Bis-(4-methoxyphenyl)-6,11-difluoro-13,13-dimethyl-3H,13H-indeno[2,1-f]naphtho[1,2-b]pyran (3.0 g) the product of Example 1 of U.S. Pat. No. 7,557,751 the disclosure of which is incorporated herein by reference, was added in portions over a 5-minute period to the reaction mixture. The color of the reaction mixture turned to deep brown and then deep green. The resulting reaction mixture was stirred at room temperature for 4 hours and morpholine (2.0 grams) and 10.0 mL of n-butyl lithium (2.5 M in hexanes) were added. The resulting reaction mixture was refluxed for about 64 hours. After cooling to room temperature, the reaction mixture was poured into 400 mL of a saturated NaCl aqueous solution and diethyl ether (200 mL) and 10% hydrochloric acid solution (20 mL) were added. The resulting mixture was extracted with ethyl acetate (2 times with 100 mL each time). The recovered organic layers were combined, washed with a saturated NaCl aqueous solution (400 mL) and dried over anhydrous sodium sulfate. The solvent was removed by rotary evaporation to yield a greenish oil that foamed upon drying under vacuum. This material was purified by column chromatography (50% hexanes, 40% methylene chloride and 10% ethyl acetate as the eluant). The fractions were analyzed by TLC and HPLC. The pure fractions were combined, solvent was removed by rotary evaporation and dried under vacuum to provide product (1.0 g). The structure was confirmed by 1H NMR and Mass Spectrometry analysis to be the desired product, 3,3-bis-(4-methoxyphenyl)-6-morpholino-11-fluoro-13,13-dimethyl-3H,13H-indeno[2,1-f]naphtho[1,2-b]pyran.

Example 4

Morpholine (4.60 grams, 2.0 eq.) was weighed into a 500 mL dry reaction flask. dTHF (200 mL) was added to the reaction flask and stirred under a nitrogen atmosphere at room temperature. n-Butyl lithium (2.0 M in hexanes, 21 mL) was added dropwise to the reaction mixture over a 10-minute period. 3-(4-Morpholinophenyl)-3-phenyl-6,11-difluoro-13,13-dimethyl-3H,13H-indeno[2',3':3,4]naphtho[1,2-b]pyran (15.0 grams) the product of Example 3 of U.S. Pat. No.

7,556,751, which disclosure is incorporated herein by reference, was added in portions over a 5-minute period to the reaction mixture. The color of the reaction mixture turned to deep green. The resulting mixture was heated for 3 hours at 45° C. After cooling to room temperature, the reaction mixture was poured into 250 mL of saturated NaCl aqueous solution. Diethyl ether (100 mL) and 20 mL of 10% hydrochloric acid solution were added and the resulting mixture was extracted with 200 mL of ethyl acetate. The recovered organic layers were combined, washed with saturated NaCl solution (1×400 mL) and dried over anhydrous sodium sulfate. The solvent was removed by rotary evaporation to yield a greenish oil that foamed upon drying. This material was purified by column chromatography (50% ethyl acetate in hexanes as the starting eluant). The fractions were analyzed by TLC and HPLC. The pure fractions were combined, the solvent was removed by rotary evaporation, and dried under vacuum. The structures were confirmed by NMR and Mass Spectrometry analysis to be 3-(4-morpholinphenyl-3-phenyl)-6,11-bismorpholino-13,13-dimethyl-3H,13H-indeno[2,1-f]naphtho[1,2-b]pyran (7 g) and the desired product of this Example 4,3-(4-morpholinphenyl-3-phenyl)-6-morpholino-11-fluoro-13,13-dimethyl-3H,13H-indeno[2,1-f]naphtho[1,2-b]pyran (3.4 g).

Example 5

Piperidine (1.87 grams, 1.20 eq.) was weighed into a 500 mL dry reaction flask. dTHF (200 mL) was added to the reaction flask and stirred under a nitrogen atmosphere at room temperature. n-Butyl lithium (2.5 M in hexanes, 8.8 mL) was added dropwise to the reaction mixture over a 5 minute period. The product of Example 1 of U.S. Pat. No. 7,556,751, 3,3-bis-(4-methoxyphenyl)-6,11-difluoro-13,13-dimethyl-3H,13H-indeno[2,1-f]naphtho[1,2-b]pyran (10 g), was added in portions over a 5-minute period to the reaction mixture. The color of the reaction mixture turned to deep brown and then deep green. The resulting mixture was stirred at room temperature. After 4 hours, piperidine (0.47 grams, 0.25 eq.) and 2.2 mL (0.25 eq.) of butyl lithium (2.5 M in hexanes) were added to the reaction mixture and stirred for about 64 hours. After cooling to room temperature, the reaction mixture was poured into 400 mL of saturated NaCl aqueous solution. Diethyl ether (200 mL) and 20 mL of 10% hydrochloric acid solution were added and the resulting mixture was extracted with 200 mL of ethyl acetate. The recovered organic layers were combined, washed with saturated NaCl aqueous solution (400 mL) and dried over anhydrous sodium sulfate. The solvent was removed by rotary evaporation to yield a greenish oil that foamed upon drying. This material was purified by column chromatography (40% hexanes, 30% methylene chloride and 30% ethyl acetate in as the eluant). The fractions were analyzed by TLC and HPLC. The pure fractions were combined, the solvent removed by rotary evaporation, and dried under vacuum. The structures were confirmed by NMR and Mass Spectrometry analysis to be 3,3-bis-(4-methoxyphenyl)-6,11-bispiperidino-13,13-dimethyl-3H,13H-indeno[2,1-f]naphtho[1,2-b]pyran (3.1 g) and the desired product of this Example 5, 3,3-bis-(4-methoxyphenyl)-6-piperidino-11-fluoro-13,13-dimethyl-3H,13H-indeno[2,1-f]naphtho[1,2-b]pyran (3.4 g).

Comparative Example 1

Step 1

Methylene chloride (2 liters (L)), 1,4-dihydroxy-2-phenoxycarbonyl-naphthalene (384 grams) and 152 grams of dihydropyran were added to a 3 L multi-necked flask at room temperature. The mixture was placed on a magnetic stirrer, and a solution of dodecylbenzenesulfonic acid (1.4 grams, in 15 milliliters (mL) of methylene chloride) was added with stirring. After 1 hour of mixing, the completed reaction was quenched by adding triethylamine (2.7 grams) and potassium carbonate (2.7 grams). The suspension was vacuum filtered and the solvent was removed by rotary evaporation. The recovered product was a thick oil. All of it was used as is, without purification, in the next step.

Step 2

The oily product from Step 1 was added to a flask and dissolved in acetone (750 mL). Potassium carbonate (200 grams) and iodomethane (220 mL) were added and the reaction was stirred and heated to 40° C. The reaction was gradually heated to reflux and iodomethane was added 4 times, each time with 1 equivalent, until the reaction was complete. The mixture was vacuum filtered and the solvent was removed by rotary evaporation to yield a concentrated liquid. The liquid was poured into 2 L of water and formed a brown precipitate. The brown precipitate was vacuum filtered, dissolved in 2.5 L of ethyl acetate and the solvent was removed by rotary evaporation to yield 200 mL of solution. The solution was poured into 3:1 hexane:ethyl acetate to induce crystallization. Brown crystals (420 grams) of product were collected. A nuclear magnetic resonance (NMR) spectrum showed the product to have a structure consistent with 4-tetrahydropyranyloxy-1-methoxy-2-phenoxycarbonyl naphthalene.

Step 3

The product of Step 2,4-tetrahydropyranyloxy-1-methoxy-2-phenoxycarbonyl naphthalene (200 grams) and tetrahydrofuran (800 mL) were added to a 3 L multi-necked flask and stirred at 0° C. under a nitrogen blanket. To the reaction mixture was added a 1 molar (M) fluorophenylmagnesium bromide solution (690 mL) drop-wise over a 1 hour period. After an additional 4.5 hours of stirring, the reaction mixture was poured into 1.5 L of water and acidified to pH 2. After individual phase layers formed, the layers were separated and the aqueous layer was extracted 2 times, each with 200 mL of ethyl acetate. The organic layers were combined, washed with water and the solvent was removed by rotary evaporation to yield a wet red solid. The red solid was added to a flask containing methanol (500 mL) and 12.1 M hydrochloric acid (5 mL), and the resulting solution was heated to reflux for 1 hour. After cooling and setting about 20 hours, the crystals that formed were collected by vacuum filtration and washed with hexane to yield 102 grams of reddish-orange crystals. An NMR spectrum showed the product to have a structure consistent with 4-hydroxy-1-(4-fluorophenyl)-2-phenoxycarbonyl naphthalene.

Step 4

The product of Step 3,4-hydroxy-1-(4-fluorophenyl)-2-phenoxycarbonyl naphthalene (148 grams) and anhydrous THF (500 mL) were added to a 3 L multi-necked flask and placed on magnetic stirrer under nitrogen and stirred. The solution was cooled to 0° C. and a 1.6 M methyl lithium solution (1.05 L) was added over 1 hour with stirring. After an additional 1.5 hours of stirring, the completed reaction was poured into 2 L of ice water and allowed to set overnight. The resulting mixture was acidified to pH 4 and the phases that formed into layers were separated. The aqueous layer was extracted 3 times, each with 200 mL of ethyl acetate. The organic layers were combined, washed with water and the solvent was removed by rotary evaporation to yield 132 g of a dark oil. The material was used directly in the next step.

Step 5

The product from Step 4 (132 grams), xylenes (1.5 L) and dodecylbenzenesulfonic acid (9.2 grams) were added to a flask and heated to reflux. After 5 hours, the reaction mixture was cooled to room temperature and washed with a 5 weight percent solution of sodium bicarbonate (300 mL). The resulting emulsion was allowed to set overnight and the phase layers that formed were separated. The organic layer was dried over magnesium sulfate and the solvent was removed by rotary evaporation to yield a concentrated liquid. The concentrated liquid was eluted through a small silica plug column with 30:1 hexane:ethyl acetate. The solvent was removed from the resulting eluant by rotary evaporation to yield an oil. Crystallization was induced with toluene and hexane to yield 28 grams of a light tan product. An NMR spectrum showed the product to have a structure consistent with 7,7-dimethyl-5-hydroxy-9-fluoro-7H-benzo[C]fluorene.

Step 6

7,7-Dimethyl-5-hydroxy-9-fluoro-7H-benzo[C]fluorene (2 grams) from Step 6, 1,1-di(4-methoxyphenyl)-2-propyn-1-ol (2 grams), two drops of dodecylbenzene sulfonic acid and chloroform (50 mL) were combined in a reaction vessel and stirred at ambient temperature for about 20 hours. Water (100 mL) was added to the reaction mixture and stirred for 30 minutes. The organic layer was separated and washed with a 10 weight percent sodium hydroxide solution followed by a wash with water. The organic layer was dried over magnesium sulfate and the solvent was removed by rotary evaporation to yield a residue. The residue was chromatographed on a silica gel using chloroform as the eluant. Photochromic fractions were collected, concentrated by rotary evaporation and the resulting solid was recrystallized from diethyl ether. An NMR spectrum showed the product to have a structure consistent with 3,3-di(4-methoxyphenyl)-11-fluoro-13,13-dimethyl-3H,13H-indeno[2',3':3,4]naphtho[1,2-b]pyran.

Comparative Example 2

3-(4-Morpholinophenyl)-3-phenyl-6-bromo-13,13-dimethyl-3H,13H-indeno[2,1-f]naphtho[1,2-b]pyran, Example 21 of U.S. Pat. No. 7,556,751 prepared using the methods described therein and incorporated herein by reference (1.5 g) was weighed into a 100 mL 3-necked reaction flask. Toluene (60 mL) was added to the reaction flask, followed by addition of morpholine (0.4 g), potassium hydroxyl (0.3 g), water (0.1 g), and hexadecyltrimethylamonium bromide (0.01 g). Nitrogen was bubbled through the reaction mixture for 10 minutes. The catalyst Bis(tri-t-butylphosphine) palladium (0) (0.02 g) was added to the reaction mixture. The mixture was heated to 90° C. and stirred at 90° C. for 6 hours. The reaction mixture was cooled to room temperature and quenched with water (20 mL). The product was extracted with ethyl acetate (3×20 mL). The recovered organic extractions were combined and dried over anhydrous sodium sulfate. The solvent was removed by rotary evaporation to yield the product. This material was purified by column chromatography (70% hexanes and 30% ethyl acetate as the eluant). The pure fractions were combined; solvent was removed by rotary evaporation, and dried under vacuum to provide the product (0.3 g). The structure was confirmed by NMR and Mass Spectrometry analysis to be the desired product, 3-(4-morpholinophenyl)-3-phenyl-6-morpholino-13,13-dimethyl-3H,13H-indeno[2,1-f]naphtho[1,2-b]pyran.

Part 2—Photochromic Property Testing

Part 2A —Test Square Preparation

Testing was done with the compounds described in Examples 1-6, and CE 1 in the following manner. A quantity of compound calculated to yield a 1.5×10$^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). Each compound was dissolved into the monomer blend by stirring and gentle heating, if necessary. After a clear solution was obtained, the sample was degassed in a vacuum oven for 5-10 minutes at 25 torr. Using a syringe, the sample was poured into a flat sheet mold having an interior dimension of 2.2 mm+/−0.3 mm×6 inch (15.24 cm)×6 inch (15.24 cm). The mold was sealed and placed in a horizontal airflow, programmable oven to ramp from 40° C. to 95° C. over a 5 hour interval, hold the temperature at 95° C. for 3 hours, ramp down to 60° C. over a 2 hour interval and then hold at 60° C. for 16 hours. After curing, the mold was opened, and the polymer sheet was cut into 2 inch (5.1 cm) test squares using a diamond blade saw.

Part 2B—Response Testing

Prior to response testing on an optical bench, the test squares from Part 2A were conditioned by exposing them to 365 nm ultraviolet light for 10 minutes at a distance of about 14 cm from the source in order to pre-activate the photochromic compounds in samples. The UVA irradiance at the sample surface was measured with a Licor Model Li-1800 spectroradiometer and found to be 22.2 Watts per square meter. The samples were then placed under a halogen lamp (500 W, 120V) for about 10 minutes at a distance of about 36 cm from the lamp in order to bleach, or inactivate, the photochromic compounds in the samples. The illuminance at the sample was measured with the Licor spectroradiometer and found to be 21.9 Klux. The samples were then kept in a dark environment for at least 1 hour prior to testing in order to cool and continue to fade back to a ground state.

The optical bench was fitted with an Newport Model #67005 300-watt Xenon arc lamp, and Model 69911 power supply, Vincent Associates (model VS25S2ZM0R3 with VMM-D4 controller) high-speed computer controlled shutter, a Schott 3 mm KG-2 band-pass filter, which removed short wavelength radiation, neutral density filter(s) to attenuate light from the xenon lamp, a fused silica condensing lens for beam collimation, and a fused silica water cell/sample holder for maintaining sample temperature in which the test sample to be tested was inserted. The temperature in the water cell was controlled with a pumped water circulation system in which the water passed through copper coils that were placed in the reservoir of a chiller unit. The water cell used to hold test samples contained fused silica sheets on the front and back facings in order to eliminate spectral change of the activation or monitoring light beams. The filtered water passing through the water cell was maintained at 72° F.±2° for photochromic response testing. A Newport Model 689456 Digital Exposure Timer was used to control the intensity of the xenon arc lamp during activation of the sample.

A broadband light source for monitoring response measurements was positioned in a perpendicular manner to a surface of the cell assembly. Increased signal of shorter visible wavelengths was obtained by collecting and combining separately filtered light from a 100-Watt tungsten halogen lamp (controlled by a Lambda UP60-14 constant voltage powder supply) with a split-end, bifurcated fiber optical cable. Light from one side of the tungsten halogen lamp was filtered with a Schott KG1 filter to absorb heat and a Hoya B-440 filter to allow passage of the shorter wavelengths. The other side of the light was either filtered with a Schott KG1 filter or unfiltered. The light was collected by focusing light from each side of the lamp onto a separate end of the split-end, bifurcated fiber optic cable, and subsequently combined into one light source emerging from the single end of the cable. A 4" light pipe was attached to the single end of the cable to insure proper mixing. After passing through the sample, the light was refocused into a 2-inch integrating sphere and fed to an Ocean Optics S2000 spectrophotometer by fiber optic cables. Ocean Optics SpectraSuite and PPG proprietary software were used to measure response and control the operation of the optical bench.

Irradiance for response testing of the samples on the optical bench was established at the sample surface using an International Light Research Radiometer, Model IL-1700 with a detector system comprising a Model SED033 detector, B Filter and diffuser. The output display of the radiometer was corrected (factor values set) against a Licor 1800-02 Optical Calibration Calibrator in order to display values representing Watts per square meter UVA. The irradiance at the sample point for initial response testing was set at to 3.0 Watts per square meter UVA and approximately 8.6 Klux illuminance. During sample response testing, if a sample darkened beyond an acceptable detection capability limit, the irradiance was lowered to 1.0 Watts per square meter UVA or the sample was remade at a one-half concentration in the copolymer. Adjusting the output of the filtered xenon arc lamp was accomplished by increasing or decreasing the current to the lamp through the controller and/or by adding or removing neutral density filters in the light path. The test samples were exposed to the activation light at 31° normal to its surface while being perpendicular to the monitoring light.

Samples were activated in the 73° F. (22.8° C.) controlled water cell for 30 minutes, then allowed to fade under room light conditions until the change in optical density of the activated sample faded to ¼ of its highest dark (saturated) state or for a maximum of 30 minutes of fade.

Change in optical density (ΔOD) from the bleached state to the darkened state was determined by establishing the initial transmittance, opening the shutter from the Xenon lamp to provide ultraviolet radiation to change the test lens from the bleached state to an activated (i.e., darkened) state. Data was collected at selected intervals of time, measuring the transmittance in the activated state, and calculating the change in optical density according to the formula: ΔOD=log(% Tb/% Ta), where % Tb is the percent transmittance in the bleached state, % Ta is the percent transmittance in the activated state and the logarithm is to the base 10.

The $\lambda_{max\text{-}vis}$ in the visible light range is the wavelength in the visible spectrum at which the maximum absorption of the activated form of the photochromic compound occurs. The $\lambda_{max\text{-}vis}$ was determined by testing the photochromic test square in a Varian Cary 4000 UV-Visible spectrophotometer or comparable equipment.

The ΔOD/Min, which represents the sensitivity of the photochromic compound's response to UV light, was measured over the first five (5) seconds of UV exposure, then expressed on a per minute basis. The saturation optical density (ΔOD at saturation) was taken under identical conditions except UV exposure was continued for a total of 30 minutes. The fade half life is the time interval in seconds for the ΔOD of the activated form of the photochromic compound in the test squares to reach one half the ΔOD measured after thirty minutes, or after saturation or near-saturation was achieved, at room temperature after removal of the source of activating light, e.g., by closing the shutter. Results are listed in Table I.

The Average Absorption Results listed in Table 2 were determined using the Varian Cary 4000 UV-Visible spectrophotometer by obtaining a simple average of the absorption values between 400 and 420 nm collected using the following values in the method: range=800-275 nm; ave. time.=0.100 s; data interval=1.100; and scan rate=660 nm/min.

TABLE 1

Photochromic Performance Test Results

| Example # | $\lambda_{max\text{-}vis}$ (nm) | Sensitivity (ΔOD/Min) | ΔOD at saturation | T½ (sec) |
|---|---|---|---|---|
| 1 | 606 | 0.180 | 0.484 | 328 |
| 2 | 614 | 0.168 | 0.492 | 374 |
| 3 | 604 | 0.216 | 0.498 | 302 |
| 4 | 617 | 0.180 | 0.814 | 596 |
| 5 | 615 | 0.192 | 0.555 | 426 |
| CE 1 | 556 | 0.192 | 0.353 | 130 |
| CE 2 | 617 | 0.192 | 0.994 | 590 |

TABLE 2

Average Absorption Results for 400 to 420 nm

| Example # | AVERAGE ABSORPTION RESULTS |
|---|---|
| 1 | 1.778 |
| 2 | 1.672 |
| 3 | 1.790 |
| 4 | 1.680 |
| 5 | 1.674 |
| CE 1 | 0.432 |
| CE 2 | 2.061 |

The present invention has been described with reference to specific details of particular embodiments thereof. It is not intended that such details be regarded as limitations upon the scope of the invention except insofar as and to the extent that they are included in the accompanying claims.

What is claimed is:

1. A photochromic material comprising, an indeno-fused naphthopyran having the following structural formula:

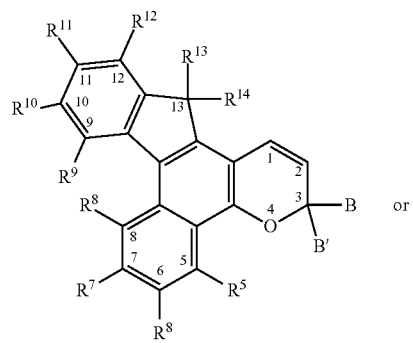

Formula-(I)

-continued

Formula-(II)

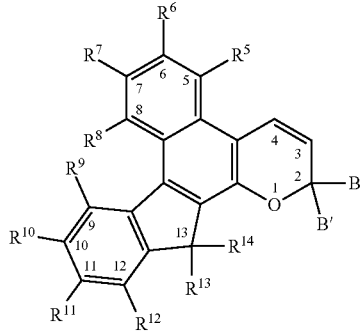

wherein $R^6$ represents an amino group, the amine-nitrogen of said amino group being bonded to the said 6-position of said indeno-fused naphthopyran, said amino group being selected from the group consisting of secondary amines and tertiary amines, and $R^{11}$ represents halo group bonded to the 11-position of said indeno-fused naphthopyran, wherein the 13-position of said indeno-fused naphthopyran is substantially free of spiro-substituents, and perhalo groups.

2. The photochromic material of claim 1, wherein, $R^6$ is selected from the group consisting of:

(1) —N($R_{15}$)$R_{16}$ wherein $R_{15}$ and $R_{16}$ are each selected from the group consisting of hydrogen provided that only one of $R_{15}$ and $R_{16}$ is hydrogen, $C_1$-$C_{12}$alkyl, phenyl, naphthyl, heteroaromatic groups, furanyl, benzofuran-2-yl, benzofuran-3-yl, thienyl, benzothien-2-yl, benzothien-3-yl, dibenzofuranyl, dibenzothienyl, benzopyridyl and fluorenyl, $C_1$-$C_{12}$alkylaryl, $C_3$-$C_{20}$ cycloalkyl, $C_4$-$C_{20}$ bicycloalkyl, $C_5$-$C_{20}$ tricycloalkyl and $C_1$-$C_{20}$ alkoxyalkyl, wherein said aryl group is phenyl or naphthyl;

(2) a nitrogen containing ring represented by the following graphic formula,

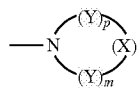

wherein Y is independently selected for each p and each m from the group consisting of —$CH_2$—, —$CH(R_{17})$—, —$C(R_{17})(R_{17})$—, —CH(aryl)-, —C(aryl)$_2$-, and —C($R_{17}$)(aryl)-, and X is selected from the group consisting of —Y—, —O—, —S—, —S(O)—, —S(O$_2$)—, —NH—, —N$R_{17}$— and —N-aryl, wherein $R_{17}$ is in each instance independently selected from $C_1$-$C_{12}$alkyl, said aryl substituent is phenyl or naphthyl, m is the integer 1, 2 or 3, and p is the integer 0, 1, 2, or 3, provided that when p is 0, X is Y; and (3) a group represented by the following graphic formulae:

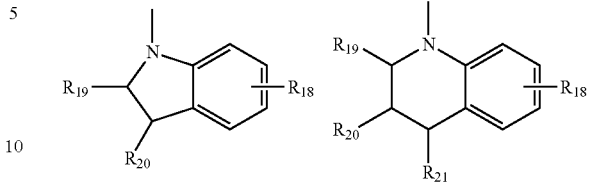

wherein $R_{19}$, $R_{20}$ and $R_{21}$ are each hydrogen, $C_1$-$C_{12}$alkyl, phenyl or naphthyl, or the groups $R_{19}$ and $R_{20}$ together form a ring of 5 to 8 carbon atoms, and $R_{18}$ is $C_1$-$C_{12}$alkyl, $C_1$-$C_{12}$alkoxy, fluoro or chloro.

3. The photochromic material of claim 2, wherein $R^6$ is selected from the group consisting of substituted or unsubstituted piperidenyl, and substituted or unsubstituted morpholinyl.

4. The photochromic material of claim 3 wherein said halo group bonded to the 11-position of said indeno-fused naphthopyran is fluoro.

5. The photochromic material of claim 1, wherein said halo group bonded to the 11-position of said indeno-fused naphthopyran is selected from the group consisting of fluoro, chloro, bromo and iodo.

6. The photochromic material of claim 5, wherein said halo group bonded to the 11-position of said indeno-fused naphthopyran is fluoro.

7. The photochromic material of claim 1, wherein said amino group $R^6$ bonded to the 6-position of said indeno-fused naphthopyran is selected from the group consisting of:

(1) —N($R_{15}$)$R_{16}$ wherein $R_{15}$ and $R_{16}$ are each selected from the group consisting of hydrogen provided that only one of $R_{15}$ and $R_{16}$ is hydrogen, $C_1$-$C_{12}$alkyl, phenyl, naphthyl, heteroaromatic groups, furanyl, benzofuran-2-yl, benzofuran-3-yl, thienyl, benzothien-2-yl, benzothien-3-yl, dibenzofuranyl, dibenzothienyl, benzopyridyl and fluorenyl, $C_1$-$C_{12}$alkylaryl, $C_3$-$C_{20}$ cycloalkyl, $C_4$-$C_{20}$ bicycloalkyl, $C_5$-$C_{20}$ tricycloalkyl and $C_1$-$C_{20}$ alkoxyalkyl, wherein said aryl group is phenyl or naphthyl;

(2) a nitrogen containing ring represented by the following graphic formula,

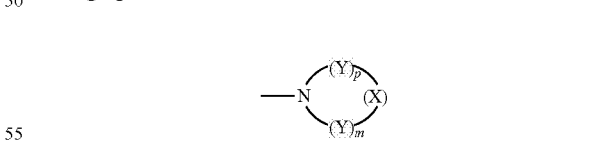

wherein Y is independently selected for each p and each m from the group consisting of —$CH_2$—, —$CH(R_{17})$—, —$C(R_{17})(R_{17})$—, —CH(aryl)-, —C(aryl)$_2$-, and —C($R_{17}$)(aryl)-, and X is selected from the group consisting of —Y—, —O—, —S—, —S(O)—, —S(O$_2$)—, —NH—, —N$R_{17}$— and —N-aryl, wherein $R_{17}$ is in each instance independently selected from $C_1$-$C_{12}$alkyl, said aryl substituent is phenyl or naphthyl, m is the integer 1, 2 or 3, and p is the integer 0, 1, 2, or 3, provided that when p is 0, X is Y; and (3) a group represented by the following graphic formulae:

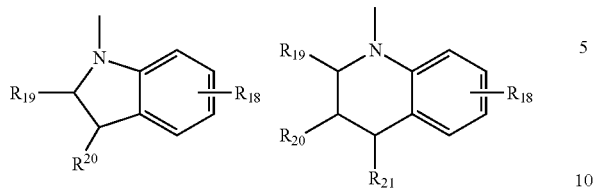

wherein $R_{19}$, $R_{20}$ and $R_{21}$ are each hydrogen, $C_1$-$C_{12}$alkyl, phenyl or naphthyl, or the groups $R_{19}$ and $R_{20}$ together form a ring of 5 to 8 carbon atoms, and $R_{18}$ is $C_1$-$C_{12}$alkyl, $C_1$-$C_{12}$alkoxy, fluoro or chloro.

8. The photochromic material of claim 7, wherein said amino group $R^6$ bonded to the 6-position of said indeno-fused naphthopyran is selected from the group consisting of substituted or unsubstituted piperidenyl, and substituted or unsubstituted morpholinyl.

9. The photochromic material of claim 8, wherein said halo group $R^{11}$ bonded to the 11-position of said indeno-fused naphthopyran is fluoro.

10. The photochromic material of claim 9, wherein $R^5$, $R^7$, $R^8$, $R^9$, $R^{10}$ and $R^{12}$ are each hydrogen,
$R^{13}$ and $R^{14}$ are each independently selected from the group consisting of $C_1$-$C_{12}$alkyl, and $C_3$-$C_7$ cycloalkyl, and
B and B' are each independently selected from the group consisting of aryl substituted with $C_1$-$C_{12}$alkoxy, and aryl substituted with morpholino.

11. The photochromic material of claim 1, wherein said halo group $R^{11}$ bonded to the 11-position of said indeno-fused naphthopyran is selected from the group consisting of fluoro, chloro, bromo and iodo.

12. The photochromic material of claim 11, wherein said halo group $R^{11}$ bonded to the 11-position of said indeno-fused naphthopyran is fluoro.

13. The photochromic material of claim 1, wherein at least one of $R^5$, $R^7$, $R^8$, $R^9$, $R^{10}$, $R^{12}$, $R^{13}$, $R^{14}$, B and B' comprises at least one of said reactive substituent and said compatibilizing substituent, further wherein said reactive substituent and said compatiblizing substituent are each independently represented in each case by one of:

| | | |
|---|---|---|
| -A'-D-E-G-J; | -G-E-G-J; | -D-E-G-J; |
| -A'-D-J; | -D-G-J; | -D-J; |
| -A'-G-J; | -G-J; and | -A'-J; | wherein:
(i) each -A'- is independently —O—, —C(=O)—, —CH₂—, —OC(=O)— or —NHC(=O)—, provided that if -A'- is —O—, -A'- forms at least one bond with -J;
(ii) each -D- is independently:
 (a) a diamine residue or a derivative thereof, said diamine residue being an aliphatic diamine residue, a cyclo aliphatic diamine residue, a diazacycloalkane residue, an azacyclo aliphatic amine residue, a diazacrown ether residue or an aromatic diamine residue, wherein a first amino nitrogen of said diamine residue forms a bond with -A'-, or a substituent or an available position on the indeno-fused naphthopyran, and a second amino nitrogen of said diamine residue forms a bond with -E-, -G- or -J; or
 (b) an amino alcohol residue or a derivative thereof, said amino alcohol residue being an aliphatic amino alcohol residue, a cyclo aliphatic amino alcohol residue, an azacyclo aliphatic alcohol residue, a diazacyclo aliphatic alcohol residue or an aromatic amino alcohol residue, wherein an amino nitrogen of said amino alcohol residue forms a bond with -A'-, or a substituent or an available position on the indeno-fused naphthopyran, and an alcohol oxygen of said amino alcohol residue forms a bond with -E-, -G- or -J, or said amino nitrogen of said amino alcohol residue forms a bond with -E-, -G- or -J, and said alcohol oxygen of said amino alcohol residue forms a bond with -A'-, or a substituent or an available position on the indeno-fused naphthopyran;
(iii) each -E- is independently a dicarboxylic acid residue or a derivative thereof, said dicarboxylic acid residue being an aliphatic dicarboxylic acid residue, a cycloaliphatic dicarboxylic acid residue or an aromatic dicarboxylic acid residue, wherein a first carbonyl group of said dicarboxylic acid residue forms a bond with -G- or -D-, and a second carbonyl group of said dicarboxylic acid residue forms a bond with -G-;
(iv) each -G- is independently:
 (a) —[(OC₂H₄)ₓ(OC₃H₆)ᵧ(OC₄H₈)_z]—O—, wherein x, y and z are each independently chosen and range from 0 to 50, and a sum of x, y, and z ranges from 1 to 50;
 (b) a polyol residue or a derivative thereof, said polyol residue being an aliphatic polyol residue, a cyclo aliphatic polyol residue or an aromatic polyol residue, wherein a first polyol oxygen of said polyol residue forms a bond with -A'-, -D-, -E-, or a substituent or an available position on the indeno-fused naphthopyran, and a second polyol oxygen of said polyol forms a bond with -E- or -J; or
 (c) a combination thereof, wherein the first polyol oxygen of the polyol residue forms a bond with a group —[(OC₂H₄)ₓ(OC₃H₆)ᵧ(OC₄H₈)_z]— and the second polyol oxygen forms a bond with -E- or -J; and
(v) each -J is independently:
 (a) a group —K, wherein —K is —CH₂COOH, —CH(CH₃)COOH, —C(O)(CH₂)_wCOOH, —C₆H₄SO₃H, —C₅H₁₀SO₃H, —C₄H₈SO₃H, —C₃H₆SO₃H, —C₂H₄SO₃H or —SO₃H, wherein w ranges from 1 to 18;
 (b) hydrogen, provided that if -J is hydrogen, -J is bonded to an oxygen of -D- or -G-, or a nitrogen of -D-; or
 (c) a group -L or residue thereof, wherein -L is acryl, methacryl, crotyl, 2-(methacryloxy)ethylcarbamyl, 2-(methacryloxy)ethoxycarbonyl, 4-vinylphenyl, vinyl, 1-chlorovinyl or epoxy.

14. The photochromic material of claim 1, wherein said indeno-fused naphthopyran is selected from the group consisting of,
3,3-bis-(4-methoxyphenyl)-6-morpholino-11-fluoro-13,13-dimethyl-3H,13H-indeno[2,1-f]naphtho[1,2-b]pyran,
3-(4-methoxyphenyl-3-(4-(2-hydroxyethoxy)-phenyl)-6-morpholino-11-fluoro-13,13-dimethyl-3H,13H-indeno[2,1-f]naphtho[1,2-b]pyran, 3-(4-morpholinophenyl-3-phenyl)-6-morpholino-11-fluoro-13,13-dimethyl-3H,13H-indeno[2,1-f]naphtho[1,2-b]pyran, 3,3-bis-(4-methoxyphenyl)-6-piperidino-11-fluoro-13,13-dimethyl-3H,13H-indeno[2,1-f]naphtho[1,2-b]pyran, 3-(4-methoxyphenyl-3-(4-(2-hydroxyethoxy)phenyl)-6-(3-methylmorpholino)-11-fluoro-13,13-dimethyl-3H,13H-indeno[2,1-f]naphtho[1,2-b]pyran, and combinations of two or more thereof.

15. The photochromic material of claim 1, wherein said photochromic material displays hyperchromic absorption of electromagnetic radiation having a wavelength from 320 nm to 440 nm, as compared to a comparative photochromic material comprising a comparable indeno-fused naphthopyran that is substantially free of said amino group bonded to the 6-position, and said halo group bonded to the 11-position of said comparable indeno-fused naphthopyran.

16. An optical element comprising the indeno-fused naphthopyran of claim 1.

17. The optical element of claim 16, wherein said optical element is adapted for use behind a substrate that blocks a substantial portion of electromagnetic radiation in the range of 320 nm to 390 nm, and further wherein at least a portion of said optical element absorbs at least a sufficient amount of electromagnetic radiation having a wavelength greater than 390 nm passing through said substrate that blocks said substantial portion of electromagnetic radiation in the range of 320 nm to 390 nm, such that at least a portion of said optical element transforms from a first state to a second state, wherein said first state of said optical element is a bleached state, and said second state of said optical element is a colored state.

* * * * *